(12) United States Patent
Bernstein et al.

(10) Patent No.: US 6,183,961 B1
(45) Date of Patent: Feb. 6, 2001

(54) METHODS AND COMPOSITIONS FOR REGULATING CELL CYCLE PROGRESSION

(75) Inventors: Harold S. Bernstein, San Francisco; Shaun R. Coughlin, Tiburon, both of CA (US)

(73) Assignee: The Regents of the University of California, Oakland, CA (US)

( * ) Notice: Under 35 U.S.C. 154(b), the term of this patent shall be extended for 0 days.

(21) Appl. No.: 09/156,316

(22) Filed: Sep. 18, 1998

Related U.S. Application Data

(60) Provisional application No. 60/060,688, filed on Sep. 22, 1997.

(51) Int. Cl.⁷ .............................. C12Q 1/68; C07H 21/04; C12N 15/63
(52) U.S. Cl. ......................... 435/6; 435/320.1; 435/325; 435/357; 435/365; 435/372.3; 536/23.5; 536/24.31; 536/24.33; 536/24.5
(58) Field of Search ..................... 435/6, 320.1, 325.357, 435/365, 372.3; 536/23.1, 23.5, 24.31, 24.33, 24.5

(56) References Cited

FOREIGN PATENT DOCUMENTS

WO 95/14772 * 6/1995 (WO).

OTHER PUBLICATIONS

Bernstein et al., J. Biol. Chem. 272:5833–5837 (1997).
Hirayama et al., Proc. Natl' Acad. Sci. 93:13371 (1996).
Ohi et al. EMBO J. 13:471–483 (1994).
Stukenberg et al., Curr. Biol. 7:338 (1997).
Wilson et al., Nature 368:32–38 (1994).
GenBank Accession No. W82296, 12.9.96.
GenBank Accession No. Z49809, 11.8.97.
GenBank Accession No. D85423, 19.12.96.
GenBank Accession No. AA044750, 11.5.97.
GenBank Accession No. AA305877, 18.4.97.
GenBank Accession No. N62813, 1.3.96.
GenBank Accession No. AA576220, 9.9.97.
GenBank Accession No. AA219720, 7.2.97.
GenBank Accession No. C75554, 9.9.97.
GenBank Accession No. C75528, 9.9.97.
GenBank Accession No. AA191036, 15.1.97.
GenBank Accession No. AA249176, 11.3.97.
GenBank Accession No. T81266, 9.3.95.
GenBank Accession No. C75657, 9.9.97.
GenBank Accession No. AA361072, 21.4.97.
GenBank Accession No. F09494, 24.2.95.
GenBank Accession No. AA466838, 11.6.97.
GenBank Accession No. N74285, 19.3.96.
GenBank Accession No. AA318063, 19.4.97.
GenBank Accession No. AA509907, 8.7.97.
GenBank Accession No. T65147, 7.3.95.
GenBank Accession No. R17895, 14.4.95.
GenBank Accession No. R38882, 4.5.95.
GenBank Accession No. AA437997, 4.8.97.
GenBank Accession No. R49293, 22.5.95.
GenBank Accession No. AA269568, 26.3.97.
GenBank Accession No. AA240152, 4.3.97.
GenBank Accession No. AA068162, 6.2.97.
GenBank Accession No. Z41177, 9.11.94.
GenBank Accession No. AA483343, 14.8.97.
GenBank Accession No. AA241912, 7.3.97.
GenBank Accession No. R40873, 22.5.95.
GenBank Accession No. AA590884, 16.9.97.
GenBank Accession No. W04385, 22.4.96.
GenBank Accession No. R43141, 22.5.95.
GenBank Accession No. AA219672, 7.2.97.
GenBank Accession No. T59208, 9.2.95.
GenBank Accession No. AA555853, 13.8.97.
GenBank Accession No. T17294, 14.2.97.
GenBank Accession No. AA095444, 25.10.96.
GenBank Accession No. AA109541, 4.2.97.
GenBank Accession No. X61859, 16.9.92.
GenBank Accession No. N56376, 20.2.96.
GenBank Accession No. AA352511, 21.4.97.
GenBank Accession No. F08104, 21.2.95.
GenBank Accession No. W16278, 10.9.96.
GenBank Accession No. AA176008, 16.2.1997.
GenBank Accession No. R13357, 12.4.95.
GenBank Accession No. R34903, 2.5.95.
GenBank Accession No. F13440, 15.3.95.
GenBank Accession No. T59167, 9.2.95.
GenBank Accession No. AA073241, 7.2.97.
GenBank Accession No. T65340, 7.3.95.
GenBank Accession No. AA262453, 13.8.97.
GenBank Accession No. AA060140, 23.9.96.
GenBank Accession No. T60967, 13.2.95.
GenBank Accession No. R47097, 15.5.95.
GenBank Accession No. AA068260, 6.2.97.
GenBank Accession No. AA547602, 5.8.97.
Branch (1998) A good antisense molecule is hard to find. Trends Biol. Sci. 23:45–50, Feb. 1998.*

* cited by examiner

*Primary Examiner*—Robert A. Schwartzman
(74) *Attorney, Agent, or Firm*—Cooley Godward LLP

(57) ABSTRACT

Method and compositions for regulating cell cycle progression are disclosed. Compositions include nucleic acids comprising a human Cdc5 gene, antisense gene and fragments thereof and a human Cdc5 protein and polypeptide fragments thereof polypeptide. The compositions can be used in a method to treat diseases relating to a cell cycle defect.

18 Claims, 20 Drawing Sheets

```
MPRIMIKGGVWRNTEDEILKAAVMKYGKNQWSRIASLLHRKSAKQCKARW    50

YEWLDPSIKKTEWSREEEEKLLHLAKLMPTQWRTIAPIIGRTAAQCLEHY    100

EFLLDKAAQRDNEEETTDDPRKLKPGEIDPNPETKPARPDPIDMDEDELE    150

MLSEARARLANTQGKKAKRKAREKQLEEARRLAALQKRRELRAAGIEIQK    200

KRKRKRGVDYNAEIPFEKKPALGFYDTSEENYQALDADFRKLRQQDLDGE    250

LRSEKEGRDRKKDKQHLKRKKESDLPSAILQTSGVSEFTKKRSKLVLPAP    300

QISDAELQEVVKVGQASEIARQTAEESGITNSASSTLLSEYNVTNNSVAL    350

RTPRTPASQDRILQEAQNLMALTNVDTPLKGGLNTPLHESDFSGVTPQRQ    400

VVQTPNTVLSTPFRTPSNGAEGLTPRSGTTPKPVINSTPGRTPLRDKLNI    450

NPEDGMADYSDPSYVKQMERESREHLRLGLLGLPAPKNDFEIVLPENAEK    500

ELEEREIDDTYIEDAADVDARKQAIRDAERVKEMKRMHKAVQKDLPRPSE    550

VNETILRPLNVEPPLTDLQKSEELIKKEMITMLHYDLLHHPYEPSGNKKG    600

KTVGFGTNNSEHITYLEHNPYEKFSKEELKKAQDVLVQEMEVVKQGMSHG    650

ELSSEAYNQVWEECYSQVLYLPGQSRYTRANLASKKDRIESLEKRLEINR    700

GHMTTEAKRAAKMEKKMKILLGGYQSRAMGLMKQLNDLWDQIEQAHLELR    750

TFEELKKHEDSAIPRRLECLKEDVQRQQEREKELQHRYADLLLEKETLKS    800

```
hCdc5       IKGGVWRNTEDEILKAAVMKYGKNQWSRIASLLHRKSAKQCKARWYEWLDP  (6-56)
Spombecdc5  LKGGAWKNTEDEILKAAVSKYGKNQWARISSLLVRKTPKQCKARWYEWIDP  (5-55)
b-Myb       VK-GPWTKEEDQKVIELVKKYGTKQWTLIAKHLKGRLGKQCRERWHNHLNP  (88-137)
a-Myb       IK-GPWTKEEDQRVIELVQKYGPKRWSLIAKHLKGRIGKQCRERWHNHLNP  (87-136)
c-Myb       IK-GPWTKEEDQRVIELVQKYGPKRWSVIAKHLKGRIGKQCRERWHNHLNP  (92-141)
```

Fig. 2B

| | | |
|---|---|---|
| hCdc5 | PLKGGLNTPLHESDFSGVTPQRQVVQTPNTVLSTPFRTPSNGAEGLTPRSGTTPKPVINSTP | (378-439) |
| S. pombe cdc5 | SVTIEVRNQLMNREQSSLLGQESIPLQPGGTGYTGVT-PSHAANGS---ALAAP--Q--ATP | (380-434) |
| b-Myb | PVK-TL--PFSPSQFLNFWNKQDTLELESPSLTSTPVCSQKVVVTTPLHRDKTPLHQKHAAF | (445-503) |
| a-Myb | ILRKKRKMRVGHSPGSEL-RDGSLNDGGNMALKTPLKTPFSPSQFFNTCPGNEQLNIENPSF | (446-508) |

| | | |
|---|---|---|
| hCdc5 | GRTPLRDKLNINPEDGMADYSDPSYVKQMERESREHLRLGLLGLPAPKNDFEIVLPENAEK | (440-500) |
| S. pombe cdc5 | FRTPR-DTFSINAAAERAGR-LASE-REN-KIRLKALRELLAKLPKPKNDYEL-ME-P-R- | (435-487) |
| b-Myb | VTPDQKYSMDNTPHTP-TPFKNAKYGPLKPLPQTPHLEEDLKEVLRSEAGIELIIEDDIRP | (504-565) |
| a-Myb | TSTPICGQKAL-ITTPLHKETTPKDQKENVGFRTPTIRRSILGTPRTPTPFKNALAAQEKK | (509-569) |

Fig. 2C

5' untranslated region:

GGCACGAGAGGAAGTGGCGGCTTTGAGTCCGGTGGCCCAATCGCTGTTACTACTTCTCTGAAGCTCCTCTCGGCTGCTTGC
CGAGACACCCTGCCGCCAAG

Coding region:

1 DNA BINDING DOMAIN (_)

```
   1 atgcctcgaa ttatgatcaa ggggggcgta tggaggaata ccgaggatga aattctgaaa
  61 gcagcggtaa tgaaatatgg gaaaaatcag tggtctagga ttgcctcatt gctgcataga
 121 aaatcagcaa agcagtgcaa agccagatgg tatgaatggc tggatccaag cattaagaag
 181 acagaatggt ccagagaaga agaggaaaaa ctcttgcact tggccaagtt gatgccaact
 241 cagtggagga ccattgctcc aatcattgga agaacagcgg cccagtgctt agaacactat
 301 gaatttcttc tggataaagc tgcccaaaga gacaatgaag aggaaacaac agatgatcca
 361 cgaaaactta aacctggaga aatagatcca aatccagaaa caaaaccagc gcggcctgat
 421 ccaattgata tggatgagga tgaacttgag atgctttctg aagccagagc ccgcttggct
```

2 NUCLEAR LOCALIZATION DOMAIN (_)

```
 481 aatactcagg gaaagaaggc caagaggaaa gcaagagaga aacaattgga agaagcaaga
 541 cgtcttgctg ccctccaaaa aagaagagaa cttcgagcag ctggcataga aattcagaag
 601 aaaagaaaaa ggaagagagg agttgattat aatgccgaaa tcccatttga aaaaaagcct
 661 gcccttggtt tttatgatac ttctgaggaa aactaccaag ctcttgacgc agatttcagg
 721 aaattaagac aacaggatct tgatgggagc taagatctg aaaaagaagg aagagataga
 781 aaaaaagaca aacagcattt gaaaaggaaa aaagaatctg atttaccatc agctattctt
 841 caaactagtg gtgtttctga atttactaaa aagagaagca aactagtact tcctgcccct
 901 cagatttcag atgcagaact ccaggaagtt gtaaaagtag gccaagcgag tgaaattgca
 961 cgtcaaactg ccgaggaatc tggcataaca aattctgctt ccagtacact tttgtctgag
1021 tacaatgtca ccaacaacag cgttgctctt agaacaccac gaacaccagc ttcccaggac
1081 agaattctgc aggaagccca gaacctcatg gccctcacca atgtggacac cccattgaaa
```

3 ACTIVATING DOMAIN (_)

```
1141 ggtggactta atcccccatt gcatgagagt gacttctcag gtgtaactcc acagcgacaa
1201 gttgtacaga ctccaaacac agttctctct actccattca ggactccttc taatggagct
1261 gaagggctga ctcccgag tggaacaact cccaaccag ttattaactc tactccgggt
1321 agaactcctc ttcgagacaa gttaaacatt aatcccgagg atggaatggc agactatagt
1381 gatccctctt acgtgaagca gatggaaaga gaatcccgag aacatctccg tttagggttg
1441 ttgggccttc ctgcccctaa gaatgatttt gaaattgttc taccagaaaa tgccgagaag
1501 gagctggaag aacgtgaaat agatgatact tacattgaag atgctgctga tgtggatgct
1561 cgaaagcagg ccatacgaga tgcagagcgt gtaaaggaaa tgaaacgaat gcataaagct
1621 gtccagaaag atctgccaag accatcagaa gtaaatgaaa ctattctaag acccttaaat
1681 gtagaaccgc ctttaacaga tttacagaaa agtgaagaac taatcaaaaa agaaatgatc
1741 acaatgcttc attatgacct tctacatcac cctttatgaac catctggaaa taaaaaaggc
1801 aaaactgtag ggtttggtac caataattca gagcacatta cctatctgga acataatcct
1861 tatgaaaagt tctccaaaga agagctgaaa aaggcccagg atgtttttggt gcaggagatg
1921 gaagtggtta aacaaggaat gagccatgga gagctctcaa gtgaagctta taaccaggtg
1981 tgggaagaat gctacagtca agtttatat cttcctgggc agagccgcta cacacgggcc
2041 aatctggcta gtaaaaagga cagaattgaa tcacttgaaa agaggctcga gataaacagg
2101 ggtcacatga cgacagaagc caagagggct gcaaagatgg aaaagaagat gaaaattttg
2161 cttggggggt accagtctcg tgctatgggg ctcatgaaac agttgaatga cttatgggac
2221 caaattgaac aggctcactt ggagttacgc acttttgaag aactcaagaa acatgaagat
2281 tctgctattc cccggaggct agagtgtcta aaagaagacg ttcagcgaca acaagaaaga
2341 gaaaggaac ttcaacatag atatgctgat ttgctgctgg agaaagagac tttaaagtca
2401 aaattctga
```

3' untranslated region:

AGTACAGTTTATATTCTGTCACAGGATTAATTAATTGCCGGTTTTCATACTCTAGAAGGCTGAAACTG ATGTTTATCTTCATTGACA
AATTTACCCACCATCTGTGGTTTTTCAGTTGTTTATTTTAAATGATATCGATCTTACACATTCTGTGTATAAAGACCTTAACTCCACA
GGACGGACATTTTAGAGTTTAAATTATTA AGGCTATCATTCTTTTAGTAATGTCATATTTGCAAACTTTTTTAGTTTTTGGCCTTTAA
TTTAAAAAGCCTAATTTTAAAGTGCTGCCTGTGAGTAACTCTTGAATAAAAAACAAAATATAAAAA

Fig. 2D

… # METHODS AND COMPOSITIONS FOR REGULATING CELL CYCLE PROGRESSION

This application claims the benefit under 35 U.S.C. § 119(e) of provisional application 60/060,688, filed Sep. 22, 1997, the disclosure of which is incorporated herein by reference.

This work was supported in part by National Institutes of Health Grant Nos. HL03228, HL43821, and HL44907. The United States Government may have certain rights to this invention.

BACKGROUND OF THE INVENTION

Orchestration of the cell division cycle includes a series of checkpoints which ensure that some events are completed before others begin (Murray, A. et al. *The Cell Cycle* Oxford University Press (1993). One set of controls determines whether cells replicate their genome in preparation for division (G1/S), while another checks that DNA replication is complete and that the cell has grown sufficiently for division to take place (G2/M) (Nasmyth, K. *Science* 274: 1643–1645 (1996). Cyclins and cyclin-dependent kinases (CDKs) regulate these events in part by controlling the transcription of specific effector genes (Okayama, H. et al., *Adv. Cancer Res.* 69: 17–62 (1996); Sanchez, I et al., *Curr. Opin. Cell. Biol.* 8: 318–824 (1996)). In budding yeast, CDC28 regulates the transcription of genes whose products are needed for the G1/S transition or S phase (Andrews, B. J. et al., *J. Biol. Chem.* 265: 14057–14060 (1990); Johnston, L. H. et al., *Nucl. Acids Res.* 20: 2403–2010 (1992)) via the transcription factors SBF (Swi4–Swi6) and DSC1 (Swi6-Mbp1) (Andrews, B. J. et al., *Cell* 57: 21–29 (1989); Dirick, L. et al., *Nature* 357: 508–513 (1992); Lowndes, N. F. et al., *Nature* 357: 505–508 (1992); Lowndes, N. F. et al., *Nature* 350: 247–250 (1991); Taba, M. R. et al., *Genes Dev.* 5: 2000–2013 (1991)). In fission yeast, the SBF-related heterodimer, MBF, is required for the expression of similar genes (Aves, S. J. et al., *EMBO J.* 4: 457–463 (1985); Lowndes, N. F. et al., *Nature* 357: 505–508 (1992); Tanaka, K. et al., *EMBO J.* 11: 4923–4932 (1992)). In mammalian cells, the CDK-regulated transcription factor E2F plays a key role in regulating the G1/S transition (Muller, R., *Trends Genet.* 11: 173–178 (1995); Sanchez, I et al., *Curr Opin Cell. Biol.* 8: 318–824 (1996)). E2F is complexed with Rb until Rb phosphorylation by G1 cyclin-dependent kinases releases E2F to activate transcription of immediate early genes including myc, fos, and jun (Beijersbergen, R. L. et al., *Biochim. Biophys. Acta* 1287: 103–120 (1996)).

Similar cyclin-dependent control mechanisms regulate the G2/M transition (Forsberg, S. L. et al., *Annu. Rev. Cell. Biol.* 7: 227–256 (1991); Nurse, P., *Cell* 79: 547–550 (1994); Nurse, P., *Nature* 344: 503–508 (1990)), but less is known about their downstream targets (Stukenberg, P. T. et al., *Curr. Biol.* 7: 338–348 (1997)). In fission yeast, regulation of the Cdc2–Cdc13 cyclin-dependent kinase-cyclin complex by the Wee1 kinase and Cdc25 phosphatase is thought to be the primary mechanism controlling G2/M (Okayama, H. et al., *Adv. Cancer Res.* 69: 17–62 (1996); Russell, P. et al., *Cell* 49: 559–567 (1987)). The Cdc2–Cdc13 complex accumulates during S phase, but Cdc2 is phosphorylated and thereby maintained in an inactive state by Wee1 (Fleig, U. N. et al., *Semin. Cell. Biol.* 2: 195–205 (1991); Lundgren, K. et al., *Cell* 65: 1111–1122 (1991)). As cells complete DNA replication, Wee1 is phosphorylated by Nim1 and thereby inactivated (Russell, P. et al., *Cell* 49: 559–567 (1987)), and Cdc25 accumulation leads to the dephosphorylation of Cdc2 (Gautier, J. et al., Cell 67: 197–211 (1991); Moreno, S. et al., *Nature* 344: 549–552 (1990)). Dephosphorylation and activation of Cdc2 heralds progression through G2 and entry into mitosis. The biochemical events controlling G2/M transit in mammalian cells are remarkably similar to those in *S. pombe*. Mammalian Cdc2 kinase accumulates in S phase (Shimizu, M. et al., *Mol. Cell. Biol.* 15: 2882–2892 (1995)) and is regulated by a Wee1 kinase (Parker, L. L. et al., *Science* 257: 1955–1957 (1992)) and Cdc25 phosphatase (Honda, R. et al., *FEBS Lett.* 318: 331–334 (1993)). While G2/M progression requires the coordinated expression of many genes, how this is regulated at the level of transcription remains largely unknown. The identification and characterization of transcription factors regulating G2 progression and mitotic entry, therefore, would significantly advance our understanding of the mechanisms controlling this portion of the cell cycle.

Most mammalian cells, such as hepatocytes, reside in G0 and can re-enter the cell cycle and undergo mitosis. Significant exceptions to this general rule include skeletal and cardiac myocytes, which are terminally differentiated and apparently incapable of undergoing mitosis shortly after the postnatal period. Tam et al. disclosed the possibility that reversal of terminal differentiation in cardiac myocytes might be achieved by manipulation of pocket proteins and/or cyclin D and cdk2 expression and function (*Annals NY Acad Sci.* 752: 72–79 (1995). Kirshenbaum et al. (*J. Biol. Chem.* 270: 7791–7794 (1995)) disclosed the reactivation of DNA synthesis, but not proliferation, of cardiac myocytes by the adenoviral protein E1A in concert with E1B delivered via an adenovirus vector. Kirshenbaum et al. (*Dev. Biol.* 179: 402–411 (1996)) disclosed that E2F-1 delivered via an adenovirus vector together with E1B can also activate DNA synthesis and cause the accumulation of cardiac myocytes in G2/M.

Thus, a need exists for agents which can direct cell cycle progression through G2 and entry into mitosis. The instant invention addresses this need and more.

SUMMARY OF THE INVENTION

One aspect of the invention is an isolated nucleic acid having the sequence of FIG. 2D (SEQ ID No: 11).

A further aspect of the invention is an antisense nucleic acid comprising a nucleic acid sequence complementary to the nucleic acid sequence of FIG. 2D (SEQ ID No: 11).

A further aspect of the invention is a method for treating a cell cycle defect in patient comprising administering to cells in the patient a therapeutic amount of an hCdc5 protein.

A further aspect of the invention is a method for treating a cell cycle defect in a patient comprising administering to cells in the patient an antagonist of hCdc5.

A further aspect of the invention is a method of treating a patient having a hyperproliferative disease, comprising administering to hyperproliferative cells in the patient nucleic acid comprising an hCdc5 nucleic acid, wherein the polypeptide encoded by the nucleic acid is over-expressed, and as a result of the over-expressed polypeptide the cells die.

A further aspect of the invention is a method of regulating the progression of a cell cycle through G2 and into mitosis, comprising administering to a cell an antagonist of hCdc5.

A further aspect of the invention is a polypeptide having the amino acid sequence of FIG. 1A (SEQ ID No: 1).

BRIEF DESCRIPTION OF THE DRAWINGS

FIG. 1A depicts the amino acid sequence (SEQ ID NO: 1) of the 802-amino acid open reading frame of hCdc5 derived from HeLa cDNA clone 67.1. The thick solid underline denotes putative DNA binding domains; the thinner solid underline denotes putative nuclear localization signals; the broken underline denotes the putative activating domain. Shown are potential phosphorylation sites for casein kinase II (▼), MAP kinase (●), protein kinase A (■), and protein kinase C (♦).

FIG. 2B depicts a sequence alignment demonstrating amino-terminal homology with *S. pombe* Cdc5 (SEQ ID No: 3) and the Myb family DNA binding domain. Whereas a-, b-, and c-Myb (SEQ ID No: 5, 4 and 6 respectively) contain three tandem repeats of the helix-turn-helix motif (R1, R2, R3), hCdc5 and *S. pombe* Cdc5 contain two tandem repeats (R2, R3). R2 is shown. Identical amino acids are indicated by boxes. Gaps (–) were introduced to maximize alignment. Conserved tryptophan residues characteristic of the helix-turn-helix motif (Nelson, H. C., Curr. Opin. Genet. Der. 5: 180–189 (1995) are indicated in bold. The Val→Leu substitution in the R2 DNA binding cavity, important for DNA binding specificity in Myb-family members (Ogatak, K. et al., *Nature Structural Biology* 3: 178–187 (1996)) is indicated by ●.

FIG. 2C depicts a sequence alignment of the central, hydrophilic region of hCdc5 (SEQ ID No: 7), a putative activating domain, and the activating domains of a- and b-Myb (SEQ ID No.: 10 and 9, respectively). Prolines are highlighted in bold. Gaps (–) were introduced to maximize alignment.

FIG. 2D depicts the nucleotide sequence of hCdc5 cDNA (SEQ ID NO: 11).

DETAILED DESCRIPTION OF THE INVENTION

I. Definitions

Figure 1B:
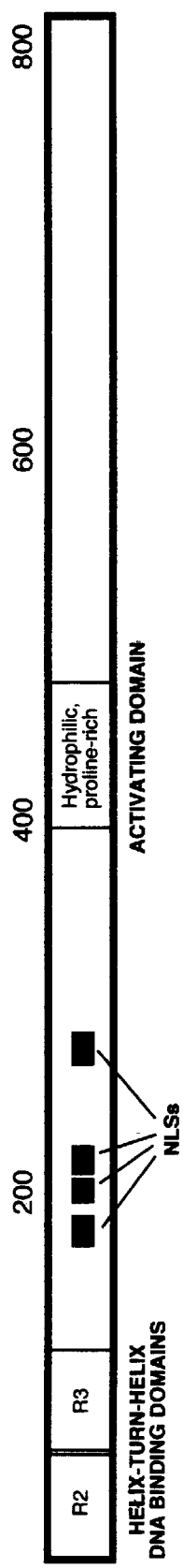
FIG. 1B is a diagram depicting the proposed functional domains of hCdc5. R2 and R3 refer to similar repeats of the helix-turn-helix DNA binding motif seen in a-, b-, and c-Myb. The amino acid number is indicated above the map. NLSs denotes nuclear localization signals.

Abbreviations for the twenty naturally occurring amino acids follow conventional usage. In the polypeptide notation used herein, the left-hand direction is the amino terminal direction and the right-hand direction is the carboxyl-terminal direction, in accordance with standard usage and convention. Similarly, unless specified otherwise, the left hand end of single-stranded polynucleotide sequences is the 5' end; the left hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "nucleic acids", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA.

"Nucleic acid probes" may be DNA or RNA fragments. DNA fragments can be prepared, for example, by digesting plasmid DNA, or by use of PCR, or synthesized by either the phosphoramidite method described by Beaucage and Carruthers, *Tetrahedron Lett.* 22: 1859– 1862 (1981), or by the triester method according to Matteucci, et al., *J. Am. Chem. Soc.* 103: 3185 (1981), both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

The phrase "selectively hybridizing to" refers to a nucleic acid probe that hybridizes, duplexes or binds only to a particular target DNA or RNA sequence when the target sequences are present in a preparation of total cellular DNA or RNA. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically.

For discussions of nucleic acid probe design and annealing conditions, see, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987).

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length protein. It being further understood that the sequence includes the degenerate codons of the native sequence or sequences which may be introduced to provide codon preference in a specific host cell.

The phrase "isolated" or "substantially pure" refers to nucleic acid preparations that lack at least one protein or nucleic acid normally associated with the nucleic acid in a host cell.

The term "operably linked" as used herein refers to linkage of a promoter upstream from a DNA sequence such that the promoter mediates transcription of the DNA sequence.

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "gene" as used herein is intended to refer to a nucleic acid sequence which encodes a polypeptide. This definition includes various sequence polymorphisms, mutations, and/or sequence variants wherein such alterations do not affect the function of the gene product. The term "gene" is intended to include not only coding sequences but also regulatory regions such as promoters, enhancers, and termination regions. The term further includes all introns and other DNA sequences spliced from the mRNA transcript, along with variants resulting from alternative splice sites.

The phrase "recombinant protein" or "recombinantly produced protein" refers to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein. The terms "protein" and "polypeptide" are used interchangeably herein.

The following terms are used to describe the sequence relationships between two or more nucleic acids or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence.

Optimal alignment of sequences for aligning a comparison window may, for example, be conducted by the local homology algorithm of Smith and Waterman *Adv. Appl. Math.* 2: 482 1981), by the homology alignment algorithm of Needleman and Wunsch *J. Mol. Biol.* 48: 443 (1970), by the search for similarity method of Pearson and Lipman *Proc. Natl. Acad. Sci. U.S.A.* 85: 2444 (1988), or by computerized implementations of these algorithms (GAP, BESTFIT, FASTA, and TFASTA in the Wisconsin Genetics Software Package Release 7.0, Genetics Computer Group, 575 Science Dr., Madison, Wis.).

The terms "substantial identity" or "substantial sequence identity" as applied to nucleic acid sequences and as used herein and denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

As applied to polypeptides, the terms "substantial identity" or "substantial sequence identity" mean that two peptide sequences, when optimally aligned, such as by the programs GAP or BESTFIT using default gap weights, share at least 80 percent sequence identity, preferably at least 90 percent sequence identity, more preferably at least 95 percent sequence identity or more. "Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "substantially purified" or "isolated" when referring to a peptide or protein, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with", when referring to a protein or peptide, refers to a binding reaction which is determinative of the presence of the protein in the presence of a heterogeneous population of proteins and other biologies. Thus, under designated immunoassay conditions, the specified antibodies bind to a particular protein and do not bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies. A Laboratory Manual,* Cold Spring Harbor Publications, New York, for a description of immunoassay formats and conditions that can be used to determine specific immunoreactivity.

II. Nucleic Acids of the Invention

The instant invention provides hCdc5 (also designated PCDC5RP) nucleic acids. The nucleic acid sequences of the invention are typically identical to or show substantial sequence identity (determined as described above) to the nucleic acid sequence of FIG. 2D (SEQ ID NO: 11). Included in this definition are nucleic acids which hybridize to the nucleic acid sequence of FIG. 2D under stringent conditions. "Stringent" as used herein refers to hybridization and wash conditions of 50% formamide at 42° C. Other stringent hybridization conditions may also be selected. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents and the extent of base mismatching, the combination of parameters is more important than the absolute measure of any one.

Oligonucleotides comprising at least 8–100 consecutive nucleotides unique to the sequence of FIG. 2D (SEQ ID NO: 11) or its complement, more preferably 15–50 consecutive nucleotides unique to the sequence of FIG. 2D (SEQ ID NO: 11) or its complement are also provided in the instant invention. Such oligonucleotides may be provided as member of primer pairs. Oligonucleotides are useful, for example, for amplification of hCdc5 sequences, whether genomic or cDNA, and in diagnostic assays.

"Wild-type" or "unaffected" hCdc5 nucleic acids are identical to or substantially identical to the sequence of FIG. 2D (SEQ ID NO: 11). These nucleic acids may comprise sequence polymorphisms, silent mutations, or other mutations which do not affect the function of the hCdc5 protein.

The nucleic acids of the inventions are useful for diagnostic assays to detect, for example, mutations in the hCdc5 gene. Such mutations may be indicative of aberrant forms of hCdc5 which have lost the ability to regulate cell cycle progression. Such mutations may cause hyperproliferation, aberrant cell size, delayed entry into mitosis, apoptosis or other cell death, or other phenotype associated with a defect in cell cycle progression. Various formats for such assays are described in detail below.

The nucleic acids of the invention are also useful in the therapy of pathologies such as diseases, syndromes, or other undesirable conditions resulting from defects in cell cycle progression. Such cell cycle defects may result from defects in the hCdc5 gene itself, in the regulation of expression of the hCdc5 gene, or in a step "downstream" of hCdc5 in the regulation of cell cycle progression through G2 and entry into mitosis. In an embodiment, nucleic acids of the invention encoding antagonists of hCdc5 are useful in preventing or delaying the progression of gametes through G2 and entry into mitosis as a form of birth control. In other embodiments, nucleic acids of the invention encoding antagonists of hCdc5 are useful in the treatment of pathologies such as but not limited to hyperproliferative diseases such as cancer (e.g., leukemia, lymphoma, breast cancer, colon cancer, prostate cancer, Wilms' tumor), coronary artery disease, pulmonary vascular obstructive disease, either primary or as a feature of Eisenmenger's syndrome, and other disorders of abnormal cellular proliferation. Cells to be treated include but are not limited to hyperproliferative cells, cancer cells, vascular smooth muscle cells, endothelial cells, gametes, etc.

In some embodiments of the invention, the nucleic acids of the invention encoding wild type protein or agonists of hCdc5 are used to stimulate, promote, or facilitate progression through the cell cycle, such as in the cellular regeneration of terminally differentiated cardiac myocytes or tissues, e.g., striated muscle myocytes. For example, this could allow restoration of damaged myocardium after cardiac injury, myocardial infarction, myocarditis, cardiomyopathy, trauma, as a consequence of cardiac surgery, etc., or repletion of striated muscle exhausted by muscular dystrophy.

The nucleic acids are typically delivered to cells by the methods described in more detail below. In some embodiments, expression of the polypeptides encoded by the nucleic acids is expected to prevent, ameliorate, or lessen the cell cycle defect of the host cell, or to restore normal cell cycle progression of the host cell. Whether provided via nucleic acid or polypeptides delivered directly to cells, the therapeutic formulations of the invention can also be used as adjuncts to other forms of therapy, including but not limited to chemotherapy, radiation therapy, and so on.

Such nucleic acids may encode the wild-type, or unaffected gene product, or may encode antagonists or agonists of hCdc5 gene in the host cell. An antagonist of hCdc5 is an agent which delays or prevents progression through G2 or entry into mitosis. An agonist of hCdc5 is an agent which promotes or facilitates progression through G2 and entry into mitosis. A therapeutic dose of an antagonist of the invention is a dose sufficient to prevent, ameliorate, or delay a host cell's progression through G2 or entry into mitosis. A therapeutic dose of an agonist of the invention is a dose sufficient to promote or facilitate host cell progression through G2 and entry into mitosis.

In some embodiments, antisense antagonists of hCdc5 expression are provided. For a review of the design considerations and use of antisense oligonucleotides, see Uhlmann et al. *Chemical Reviews* 90: 543–584 (1990) the disclosure of which is hereby incorporated by reference. The antisense oligonucleotides of the present invention may be synthesized by any of the known chemical oligonucleotide synthesis methods. Such methods are generally described, for example, in Winnacker *From Genes to Clones: Introduction to Gene Technology*, VCH Verlagsgesellschaft mbH (H. Ibelgaufts trans. 1987). Antisense oligonucleotides are advantageously prepared by utilizing any of the commercially available, automated nucleic acid synthesizers. One such device, the Applied Biosystems 380B DNA Synthesizer, utilizes β-cyanoethyl phosphoramidite chemistry.

Antisense oligonucleotides hybridizable with any portion of a hCdc5 gene may be prepared by oligonucleotide synthesis methods known to those skilled in the art. While any length oligonucleotide may be utilized in the practice of the invention, sequences shorter than 12 bases may be less specific in hybridizing to the target mRNA, may be more easily destroyed by enzymatic digestion, and may be destabilized by enzymatic digestion. Hence, oligonucleotides having 12 or more nucleotides are preferred. Long sequences, particularly sequences longer than about 40 nucleotides, may be somewhat less effective in inhibiting translation because of decreased uptake by the target cell. Thus, oligomers of 12–40 nucleotides are preferred, more preferably 15–30 nucleotides, most preferably 18–26 nucleotides. Sequences of 18–24 nucleotides are most particularly preferred.

In an embodiment of the invention, an hCdc5 polypeptide is provided to a host cell subject to overexpression in that host cell; i.e., the amount of hCdc5 produced in the host cell is substantially greater than the typical endogenous level in a host cell. Such overexpression can lead to the death of the host cell. Thus, for example, delivery of the hCdc5 nucleic acid to a host cell operably linked to a high level promoter is desired to the therapy of hyperproliferative disease such as cancer. The hCdc5 can be wild-type or unaffected, or mutant, with the requirement that such overexpression result in cell death. Similarly, excess amounts, i.e., greater than normal physiological levels of hCdc5 polypeptides can be administered to host cells to result in the death of those cells.

III. Polypeptides of the Invention

The polypeptides of the invention include the polypeptides encoded by the nucleic acid of FIG. 2D (SEQ ID NO: 11), amino acid substitutions thereof which do not affect function of the hCdc5 protein, biologically active fragments thereof, and mutants or variants thereof which can serve as agonists or antagonists of hCdc5.

The polypeptides of the invention are useful, for example, in the therapy of defects in cell cycle progression as discussed above and in screening for and isolation of co-activators, accessory proteins, or targets of the hCdc5 protein. In some embodiments, administration of a polypeptide, for example, is expected to prevent, ameliorate, or lessen the defect in cell cycle progression of the host cell, or to restore normal cell cycle progression of the host cell. Such polypeptides may comprise the full length wild-type, or unaffected gene product, fragments thereof, or agonists of hCdc5 in the host cell. Antagonists and agonists are discussed above, as are exemplary indications for treatment with the polypeptides of the invention.

The polypeptides of the invention are also useful for the generation of and screening of antibodies. Such antibodies are useful, for example, as antagonists of hCdc5 protein, in the purification of the polypeptides of the invention, and in diagnostic assays for hCdc5 protein.

IV. Agonists and Antagonists of hCdc5

As discussed above, in some embodiments of the invention, antagonists and agonists of hCdc5 are provided.

Such antagonists or agonists include but are not limited to antibodies which specifically bind to hCdc5; antibodies which specifically bind to an hCdc5 co-activator, accessory protein, or target; mutants of hCdc5 protein; antisense hCdc5 nucleic acids; co-activators or accessory proteins for hCdc5; and peptide, non-peptide, and peptidomimetic analogs of such co-activators, accessory proteins, or targets or of the hCdc5 polypeptide.

Thus, for example, an exemplary antagonist of hCdc5 is a dominant negative hCdc5 mutant such as disclosed in the experimental examples. In general, it is expected that hCdc5 mutants which retain the ability to bind to a ligand such as a target promoter but which lack other function(s) which stimulates, promotes, or facilitates progression though G2 and entry into mitosis can serve as antagonists. Thus, for example, deletion mutants which can still bind a ligand such as a promoter are expected to serve as antagonists of hCdc5. Point mutations, such as amino acid substitutions, are also useful, such as in the substitution of an amino acid otherwise subject to phosphorylation. An improperly phosphorylated protein would be expected to retain its ability to bind to a ligand such as a promoter, but would not provide some other function relevant to the progression though G2 or entry into mitosis. These mutants would thus compete with endogenous hCdc5 in the host cell for natural ligands.

Agonists of hCdc5 include the wild-type hCdc5 polypeptide and may also comprise mutants of hCdc5. For example, constitutively active mutants which do not require phosphorylation for activation may compete successfully in the cell with the endogenous hCdc5.

V. Ligands of hCdc5

As used herein, "ligand" means a molecule that is recognized by a particular protein. The agent bound by or reacting with the protein is called a "ligand", a term which is definitionally meaningful only in terms of its counterpart protein. The term "ligand" does not imply any particular molecular size or other structural or compositional feature other than that the substance in question is capable of binding or otherwise interacting with the protein. Also, a "ligand" may serve either as the natural ligand to which the hCdc5 polypeptide binds or interacts, or as a functional analogue that may act as an agonist or antagonist. Thus, the present invention provides methods for the affinity purification of ligands that interact with the hCdc5. Ligands that can be investigated by this invention include but are not restricted to, agonists and antagonists, toxins and venoms, viral epitopes, hormones, sugars, cofactors, peptides, enzyme substrates, cofactors, drugs, and proteins.

Furthermore, peptide and protein ligands can be obtained by "panning" peptide or protein libraries displayed on filamentous bacteriophage against immobilized hCdc5 protein. (For examples of techniques, see Roberts et al. (1992) Gene 121: 9–15; Dennis et al. (1995) *J Biol Chem* 270: 25411–25417; Wang et al. (1995) *J Biol Chem* 270: 12250–12256). Briefly, bound phage are eluted at low pH and amplified in host cells from which the hCdc5-binding peptide sequences can be recovered by PCR. Ligands may also be identified using the yeast two-hybrid system (Fields, S. et al., *Nature* 340: 245–247 (1989)). The hCdc5-binding peptides can then be tested for their ability to inhibit any hCdc5 activity, such as progression through G2 and entry into mitosis, binding to a promoter sequence, and so on.

VI. General Methods

The nucleic acid compositions of this invention, whether RNA, cDNA, genomic DNA, or a hybrid of the various combinations, may be isolated from natural sources, including cloned DNA, or may be synthesized in vitro. The nucleic acids claimed may be present in transformed or transfected whole cells, in a transformed or transfected cell lysate, or in a partially purified or substantially pure form.

Techniques for nucleic acid manipulation of the nucleic acid sequences of the invention such as subcloning nucleic acid sequences encoding polypeptides into expression vectors, labeling probes, DNA hybridization, and the like are described generally in Sambrook et al., *Molecular Cloning—A Laboratory Manual* (2nd Ed.), Vol. 1–3, Cold Spring Harbor Laboratory, Cold Spring Harbor, N.Y., (1989), which is incorporated herein by reference. This manual is hereinafter referred to as "Sambrook et al."

There are various methods of isolating the nucleic acid sequences of the invention. For example, DNA is isolated from a genomic or cDNA library using labeled oligonucleotide probes having sequences complementary to the sequences disclosed herein. Such probes can be used directly in hybridization assays. Alternatively probes can be designed for use in amplification techniques such as PCR.

To prepare a cDNA library, mRNA is isolated from tissue such as heart or pancreas, preferably a tissue wherein expression of the gene or gene family is likely to occur. cDNA is prepared from the mRNA and ligated into a recombinant vector. The vector is transfected into a recombinant host for propagation, screening and cloning. Methods for making and screening cDNA libraries are well known. See Gubler, U. and Hoffman, B. J. *Gene* 25: 263–269 (1983) and Sambrook et al.

For a genomic library, the DNA is extracted from tissue and either mechanically sheared or enzymatically digested to yield fragments of about 12–20kb. The fragments are then separated by gradient centrifugation from undesired sizes and are constructed in bacteriophage lambda vectors. These vectors and phage are packaged in vitro, as described in Sambrook, et al. Recombinant phage are analyzed by plaque hybridization as described in Benton and Davis, *Science* 196: 180–182 (1977). Colony hybridization is carried out as generally described in M. Grunstein et al. Proc. Natl. Acad. Sci. USA. 72: 3961–3965 (1975).

DNA of interest is identified in either cDNA or genomic libraries by its ability to hybridize with nucleic acid probes, for example on Southern blots, and these DNA regions are isolated by standard methods familiar to those of skill in the art. See Sambrook, et al.

Various methods of amplifying target sequences, such as the polymerase chain reaction, can also be used to prepare DNA encoding hCdc5 protein. Polymerase chain reaction (PCR) technology is used to amplify such nucleic acid sequences directly from mRNA, from cDNA, and from genomic libraries or cDNA libraries. The isolated sequences encoding hCdc5 protein may also be used as templates for PCR amplification.

In PCR techniques, oligonucleotide primers complementary to the two 3' borders of the DNA region to be amplified are synthesized. The polymerase chain reaction is then carried out using the two primers. See *PCR Protocols: A Guide to Methods and Applications* (Innis, M, Gelfand, D., Sninsky, J. and White, T., eds.), Academic Press, San Diego (1990). Primers can be selected to amplify the entire regions encoding a full-length sequence of interest or to amplify smaller DNA segments as desired.

PCR can be used in a variety of protocols to isolate cDNA's encoding a sequence of interest. In these protocols, appropriate primers and probes for amplifying DNA encoding a sequence of interest are generated from analysis of the DNA sequences listed herein. Once such regions are PCR-amplified, they can be sequenced and oligonucleotide probes can be prepared from the sequence obtained.

Oligonucleotides for use as probes are chemically synthesized according to the solid phase phosphoramidite triester method first described by Beaucage, S. L. and Carruthers, M. H., *Tetrahedron Lett.*, 22 (20): 1859–1862 (1981) using an automated synthesizer, as described in Needham-VanDevanter, D. R., et al, *Nucleic Acids Res.* 12: 6159–6168 (1984). Purification of oligonucleotides is by either native acrylamide gel electrophoresis or by anion-exchange HPLC as described in Pearson, J. D. and Regnier, F. E., *J. Chrom.*, 255: 137–149 (1983). The sequence of the synthetic oligonucleotide can be verified using the chemical degradation method of Maxam, A. M. and Gilbert, W., in Grossman, L. and Moldave, D., eds. Academic Press, New York, *Methods in Enzymology* 65: 499–560 1980).

A. Expression

Once DNA encoding a sequence of interest is isolated and cloned, one can express the encoded proteins in a variety of recombinantly engineered cells. It is expected that those of skill in the art are knowledgeable in the numerous expression systems available for expression of DNA encoding a protein. No attempt to describe in detail the various methods known for the expression of proteins in prokaryotes or eukaryotes is made here.

In brief summary, the expression of natural or synthetic nucleic acids encoding a sequence of interest will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of polynucleotide sequence of interest. To obtain high level expression of a cloned gene, it is desirable to construct expression plasmids which contain, at the minimum, a strong promoter to direct transcription, a ribosome binding site for translational initiation, and a transcription/translation terminator. The expression vectors may also comprise generic expression cassettes containing at least one independent terminator sequence, sequences permitting replication of the plasmid in both eukaryotes and prokaryotes, i.e., shuttle vectors, and selection markers for both prokaryotic and eukaryotic systems. See Sambrook et al. Examples of expression of hCdc5 protein in both prokaryotic and eukaryotic systems are described below.

1. Expression in Prokaryotes

A variety of procaryotic expression systems may be used to express the proteins of the invention. Examples include *E. coli*, Bacillus, Streptomyces, and the like.

It is preferred to construct expression plasmids which contain, at the minimum, a strong promoter to direct transcription, a ribosome binding site for translational initiation, and a transcription/translation terminator. Examples of regulatory regions suitable for this purpose in *E. coli* are the promoter and operator region of the *E. coli* tryptophan biosynthetic pathway as described by Yanofsky, C., *J. Bacteriol.* 158: 1018–1024 (1984) and the leftward promoter of phage lambda (Pλ) as described by Herskowitz, I. and Hagen, D., *Ann. Rev. Genet.* 14: 399–445 (1980). The inclusion of selection markers in DNA vectors transformed in *E. coli* is also useful. Examples of such markers include genes specifying resistance to ampicillin, tetracycline, or chloramphenicol. See Sambrook et al. for details concerning selection markers for use in *E. coli*.

To enhance proper folding of the expressed recombinant protein, during purification from *E. coli*, the expressed protein may first be denatured and then renatured. This can be accomplished by solubilizing the bacterially produced proteins in a chaotropic agent such as guanidine HCl and reducing all the cysteine residues with a reducing agent such as beta-mercaptoethanol. The protein is then renatured, either by slow dialysis or by gel filtration. See U.S. Pat. No. 4,511,503.

Detection of the expressed antigen is achieved by methods known in the art as radioimmunoassay, or Western blotting techniques or immunoprecipitation. Purification from *E. coli* can be achieved following procedures such as those described in U.S. Pat. No. 4,511,503.

2. Expression in Eukaryotes

A variety of eukaryotic expression systems such as yeast, insect cell lines, bird, fish, and mammalian cells, are known to those of skill in the art. As explained briefly below, a sequence of interest may be expressed in these eukaryotic systems.

Synthesis of heterologous proteins in yeast is well known. *Methods in Yeast Genetics*, Sherman, F., et al., Cold Spring Harbor Laboratory, (1982) is a well recognized work describing the various methods available to produce the protein in yeast.

Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., *Gene* 8: 17–24 (1979); Broach, et al., *Gene* 8: 121–133 (1979)).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by J. D. Beggs, *Nature* (London) 275: 104–109 (1978); and Hinnen, A., et al., *Proc. Natl. Acad. Sci. U.S.A.* 75: 1929–1933 (1978). The second procedure does not involve removal of the cell wall. Instead the cells are treated with lithium chloride or acetate and PEG and put on selective plates (Ito, H., et al., *J. Bact.* 153: 163–168 (1983)).

The proteins of the invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding the proteins of the invention can also be ligated to various expression vectors for use in transforming cell cultures of, for instance, mammalian, insect, bird or fish origin. Illustrative of cell cultures useful for the production of the polypeptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines, and various human cells such as COS cell lines, HeLa cells, myeloma cell lines, Jurkat cells, etc. Expression vectors for these cells can include expression control sequences, such as an origin of replication, a promoter (e.g., the CMV promoter, a HSV tk promoter or pgk (phosphoglycerate kinase) promoter), an enhancer (Queen et al. *Immunol. Rev.* 89: 49 (1986)), and necessary processing information sites, such as ribosome binding sites, RNA splice sites, polyadenylation sites (e.g., an SV40 large TAg poly A addition site), and transcriptional terminator sequences. Other animal cells useful for production of hCdc5 proteins are available, for instance, from the American Type Culture Collection Catalogue of Cell Lines and Hybridomas (7th edition, (1992)).

Appropriate vectors for expressing the proteins of the invention in insect cells are usually derived from the SF9 baculovirus. Suitable insect cell lines include mosquito larvae, silkworm, armyworm, moth and Drosophila cell lines such as a Schneider cell line (See Schneider *J. Embryol. Exp. Morphol.* 27: 353–365 (1987).

As indicated above, the vector, e.g., a plasmid, which is used to transform the host cell, preferably contains DNA sequences to initiate transcription and sequences to control the translation of the protein. These sequences are referred to as expression control sequences.

As with yeast, when higher animal host cells are employed, polyadenylation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, J. et al., *J. Virol.* 45: 773–781 (1983)).

Additionally, gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in *DNA Cloning vol. II a Practical Approach* Ed. D. M. Glover, IRL Press, Arlington, Va. pp. 213–238.

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and microinjection of the DNA directly into the cells.

The transformed cells are cultured by means well known in the art. *Biochemical Methods in Cell Culture and Virology,* Kuchler, R. J., Dowden, Hutchinson and Ross, Inc., (1977). The expressed polypeptides are isolated from cells grown as suspensions or as monolayers. The latter are recovered by well known mechanical, chemical or enzymatic means.

B. Purification

The proteins produced by recombinant DNA technology may be purified by standard techniques well known to those of skill in the art. Recombinantly produced proteins can be directly expressed or expressed as fusion proteins. The protein is then purified by a combination of cell lysis (e.g., sonication) and affinity chromatography. For fusion products, subsequent digestion of the fusion protein with an appropriate proteolytic enzyme releases the desired polypeptide.

The polypeptides of this invention may be purified to substantial purity by standard techniques well known in the art, including selective precipitation with such substances as ammonium sulfate, column chromatography, immunopurification methods, and others. See, for instance, R. Scopes, Protein *Purification: Principles and Practice,* Springer-Verlag: New York (1982), incorporated herein by reference. For example, antibodies may be raised to the proteins of the invention as described herein. Cell membranes are isolated from a cell line expressing the recombinant protein, the protein is extracted from the membranes and immunoprecipitated. The proteins may then be further purified by standard protein chemistry techniques as described above.

C. In Vitro Diagostic Methods

The present invention provides methods for detecting DNA or RNA encoding the proteins of the invention and for measuring the proteins by immunoassay techniques. These methods are useful for two general purposes. First, assays for detection of nucleic acids encoding the proteins of the invention are useful for the isolation of these nucleic acids from a variety of vertebrate species according to the methods described in section (B) above and by use of the nucleic acid hybridization assays described below.

The nucleic acid hybridization assays and the immunoassays described below are also useful as in vitro diagnostic assays for disorders in which alterations in the proteins of the invention or related proteins play a role.

1. Nucleic Acid-Based Diagnostic Assays

A variety of methods for specific DNA and RNA measurement using nucleic acid hybridization techniques are known to those of skill in the art. See Sambrook, et al. For example, one method for evaluating the presence or absence of the nucleic acids of the invention in a sample involves a Southern transfer. Briefly, the digested genomic DNA is run on agarose slab gels in buffer and transferred to membranes. Hybridization is carried out using the nucleic acid probes discussed above. As described above, nucleic acid probes are designed based on the nucleic acid sequences of the invention. The probes can be full length or less than the full length of the nucleic acid sequence encoding the hCdc5 protein. Shorter probes are empirically tested for specificity. Preferably nucleic acid probes are 20 bases or longer in length. (See Sambrook, et al. for methods of selecting nucleic acid probe sequences for use in nucleic acid hybridization.) Visualization of the hybridized portions allows the qualitative determination of the presence or absence of DNA encoding hCdc5 protein.

Similarly, a Northern transfer may be used for the detection of mRNA encoding the proteins of the invention. In brief, the mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of the proteins of the invention A variety of nucleic acid hybridization formats are known to those skilled in the art. For example, common formats include sandwich assays and competition or displacement assays. Hybridization techniques are generally described in *Nucleic Acid Hybridization. A Practical Approach* Ed. Hames, B. D. and Higgins, S. J., IRL Press (1985); Gall and Pardue *Proc. Natl. Acad. Sci. U.S.A.* 63: 378–383 (1969); and John, Burnsteil and Jones *Nature* 223: 582–587 (1969).

For example, sandwich assays are commercially useful hybridization assays for detecting or isolating nucleic acid sequences. Such assays utilize a "capture" nucleic acid covalently immobilized to a solid support and a labeled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P- labeled probes or the like. Other labels include ligands which bind to labeled antibodies, fluorophores, chemiluminescent agents, enzymes, and antibodies which can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The label may also allow indirect detection of the hybridization complex. For example, where the label is a hapten or antigen, the sample can be detected by using antibodies. In these systems, a signal is generated by attaching fluorescent or enzyme molecules to the antibodies or, in some cases, by attachment to a radioactive label. (Tijssen, P., "Practice and Theory of Enzyme Immunoassays," *Laboratory Techniques in Biochemistry and Molecular Biology* Burdon, R. H., van Knippenberg, P. H., Eds., Elsevier (1985), pp. 9–20.)

The sensitivity of the hybridization assays may be enhanced through use of a nucleic acid amplification system which multiplies the target nucleic acid being detected. Examples of such systems include the polymerase chain reaction (PCR) system and the ligase chain reaction (LCR) system. Other methods recently described in the art are the nucleic acid sequence based amplification (NASBA™, Cangene, Mississauga, Ontario) and Q Beta Replicase systems.

An alternative means for determining the level of expression of a gene encoding the proteins of the invention is in situ hybridization. In situ hybridization assays are well known and are generally described in Angerer et al. *Methods Enzymol.* 152: 649–660 (1987). In an in situ hybridization assay, cells are fixed to a solid support, typically a glass slide. If DNA is to be probed, the cells are denatured with heat or alkali. The cells are then contacted with a hybridization solution at a moderate temperature to permit annealing of labeled probes specific to the proteins of the invention. The probes are preferably labeled with radioisotopes or fluorescent reporters.

Methods of screening nucleic acid for mutations are well known in the art, including, but not limited to, restriction-fragment-length-polymorphism detection based on allele-specific restriction-endonuclease cleavage (Kan and Dozy *Lancet* ii: 910–912 (1978)), hybridization with allele-specific oligonucleotide probes (Wallace et al. Nucl Acids Res 6: 3543–3557 (1978)), including immobilized oligonucleotides (Saiki et al. *Proc. Natl. Acad. Sci. U.S.A.* 86: 6230–6234 (1989)) or oligonucleotide arrays (Maskos and Southern Nucl Acids Res 21: 2269–2270 (1993)), allele-specific PCR (Newton et al. Nucl Acids Res 17: 2503–2516 (1989)), mismatch-repair detection (MRD) (Faham and Cox Genome Res 5: 474–482 (1995)), binding of MutS protein (Wagner et al. *Nucl Acids Res* 23: 3944–3948 (1995), denaturing-gradient gel electrophoresis (DGGE) (Fisher and Lerman et al. *Proc. Natl. Acad. Sci. U.S.A.* 80: 1579–1583 (1983)), single-strand-conformation-polymorphism detection (Orita et al. Genomics 5: 874–879 (1983)), RNAase cleavage at mismatched base-pairs (Myers et al. *Science* 230: 1242 (1985)), chemical (Cotton et al. *Proc. Natl. Acad. Sci. U.S.A.* 85: 4397–4401 (1988)) or enzymatic (Youil et al. *Proc. Natl. Acad. Sci.* U.S.A. 92: 87–91 (1995)) cleavage of heteroduplex DNA, methods based on allele specific primer extension (Syvänen et al. *Genomics* 8: 684–692 (1990)), genetic bit analysis (GBA) (Nikiforov et al. *Nucl Acids Res* 22: 4167–4175 (1994)), the oligonucleotide-ligation assay (OLA) (Landegren et al. *Science* 241: 1077 (1988)), the allele-specific ligation chain reaction (LCR) (Barrany *Proc. Natl. Acad. Sci. U.S.A.* 88: 189–193 (1991)), gap-LCR (Abravaya et al. *Nucl Acids Res* 23: 675–682 (1995)), and radioactive and/or fluorescent DNA sequencing using standard procedures well known in the art.

D. Production of Antibodies and Development of Immunoassays

Immunoassays can be used to qualitatively or quantitatively analyze for the proteins of the invention. A general overview of the applicable technology can be found in Harlow and Lane, *Antibodies: A Laboratory Manual,* Cold Spring Harbor Pubs., N.Y. (1988), incorporated herein by reference.

1. Antibody Production

A number of immunogens may be used to produce antibodies specifically reactive with the proteins of the invention. Recombinant protein is the preferred immunogen for the production of monoclonal or polyclonal antibodies. Naturally occurring protein may also be used either in pure or impure form. Synthetic peptides made using the protein sequences described herein may also used as an immunogen for the production of antibodies to the protein. Recombinant protein can be expressed in eukaryotic or prokaryotic cells as described above, and purified as generally described above. The product is then injected into an animal capable of producing antibodies. Either monoclonal or polyclonal antibodies may be generated, for subsequent use in immunoassays to measure the protein.

Methods of production of polyclonal antibodies are known to those of skill in the art. In brief, an immunogen, preferably a purified protein, is mixed with an adjuvant and animals are immunized. The animal's immune response to the immunogen preparation is monitored by taking test bleeds and determining the titer of reactivity to the ATP-sensitive potassium channel protein. When appropriately high titers of antibody to the immunogen are obtained, blood is collected from the animal and antisera are prepared. Further fractionation of the antisera to enrich for antibodies reactive to the protein can be done if desired. (See Harlow and Lane, supra).

Monoclonal antibodies may be obtained by various techniques familiar to those skilled in the art. Briefly, spleen cells from an animal immunized with a desired antigen are immortalized, commonly by fusion with a myeloma cell (See, Kohler and Milstein, *Eur. J. Immunol.* 6: 511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al. *Science* 246: 1275–1281 (1989).

Methods of production of synthetic peptides are known to those of skill in the art. Peptides preferably at least 10 amino acids in length are synthesized corresponding to these regions and the peptides are conjugated to larger protein molecules for subsequent immunization. Preferably, peptide sequences corresponding to regions of interest of a recombinant protein of the invention is used to generate antibodies specifically immunoreactive with the protein. Production of monoclonal or polyclonal antibodies is then carried out as described above.

2. Immunoassays

A particular protein can be measured by a variety of immunoassay methods. For a review of immunological and immunoassay procedures in general, see *Basic and Clinical Immunology* 7th Edition (D. Stites and A. Terr ed.) (1991). Moreover, immunoassays can be performed in any of several configurations, which are reviewed extensively in *Enzyme Immunoassay*, E. T. Maggio, ed., CRC Press, Boca Raton, Fla. (1980); "Practice and Theory of Enzyme Immunoassays," P. Tijssen, *Laboratory Techniques in Biochemistry and Molecular Biology*, Elsevier Science Publishers B. V. Amsterdam (1985); and, Harlow and Lane, *Antibodies, A Laboratory Manual*, supra, each of which is incorporated herein by reference.

Immunoassays for measurement of the proteins of the invention can be performed by a variety of methods known to those skilled in the art. In brief, immunoassays to measure the protein can be either competitive or noncompetitive binding assays. In competitive binding assays, the sample analyte competes with a labeled analyte for specific binding sites on a capture agent bound to a solid surface. Preferably the capture agent is an antibody specifically reactive with a recombinant protein of the invention produced as described above. The concentration of labeled analyte bound to the capture agent is inversely proportional to the amount of free analyte present in the sample.

Western blot analysis can also be done to determine the presence of a protein of the invention in a sample. Electrophoresis is carried out, for example, on a tissue sample suspected of containing the protein. Following electrophoresis to separate the proteins, and transfer of the proteins to a suitable solid support such as a nitrocellulose filter, the solid support is then incubated with an antibody reactive with the protein. This antibody may be labeled, or alternatively may be it may be detected by subsequent incubation with a second labeled antibody that binds the primary antibody.

The immunoassay formats described above employ labeled assay components. The label can be in a variety of forms. The label may be coupled directly or indirectly to the desired component of the assay according to methods well known in the art. A wide variety of labels may be used. The component may be labeled by any one of several methods. Traditionally a radioactive label incorporating $^3$H, $^{125}$I, $^{35}$S, $^{14}$C, or $^{32}$p was used. Non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference.

Antibodies reactive with a particular protein can also be measured by a variety of immunoassay methods. For a review of immunological and immunoassay procedures applicable to the measurement of antibodies by immunoassay techniques, see *Basic and Clinical Immunology* 7th Edition (D. Stites and A. Terr ed.) supra, *Enzyme Immunoassay*, E. T. Maggio, ed., supra, and Harlow and Lane, *Antibodies, A Laboratory Manual*, supra.

VII. Kits

This invention also embraces kits for detecting the presence of a protein of the invention in tissue or blood samples which comprise a container containing antibodies selectively immunoreactive to the protein and instructional material for performing the test. The kit may also contain other components such as a protein of the invention, controls, buffer solutions, and secondary antibodies. Kits for detecting antibodies to a protein of the invention comprise a container containing an a protein of the invention, instructional material and may comprise other materials such as secondary antibodies and labels as described herein.

This invention further embraces diagnostic kits for detecting DNA or RNA encoding proteins of interest in tissue or blood samples which comprise nucleic probes as described herein and instructional material. The kit may also contain additional components such as labeled compounds, as described herein, for identification of duplexed nucleic acids.

VIII. Formulations

The compositions of the invention will be formulated for administration by manners known in the art acceptable for administration to a mammalian subject, preferably a human. In some embodiments of the invention, the compositions of the invention can be administered directly into a tissue by injection or into a blood vessel supplying the tissue of interest. In further embodiments of the invention the compositions of the invention are administered "locoregionally", i.e., intravesically, intralesionally, and/or topically. In other embodiments of the invention, the compositions of the invention are administered systemically by injection, inhalation, suppository, transdermal delivery, etc. In further embodiments of the invention, the compositions are administered through catheters or other devices to allow access to a remote tissue of interest, such as an internal organ. The compositions of the invention can also be administered in depot type devices, implants, or encapsulated formulations to allow slow or sustained release of the compositions.

In order to administer therapeutic agents based on, or derived from, the present invention, it will be appreciated that suitable carriers, excipients, and other agents may be incorporated into the formulations to provide improved transfer, delivery, tolerance, and the like.

A multitude of appropriate formulations can be found in the formulary known to all pharmaceutical chemists: Remington's Pharmaceutical Sciences, (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

Any of the foregoing formulations may be appropriate in treatments and therapies in accordance with the present invention, provided that the active agent in the formulation is not inactivated by the formulation and the formulation is physiologically compatible.

The quantities of active ingredient necessary for effective therapy will depend on many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of the active ingredients. Animal testing of effective doses for treatment of particular disorders will provide further predictive indication of human dosage. Various considerations are described, for example, in *Goodman and Gilman's the Pharmacological Basis of Therapeutics*, 7th Edition (1985), MacMillan Publishing Company, New York, and *Remington's Pharmaceutical Sciences* 18th Edition, (1990) Mack Publishing Co, Easton Penn. Methods for administration are discussed therein, including oral, intravenous, intraperitoneal, intramuscular, transdermal, nasal, iontophoretic administration, and the like.

The compositions of the invention may be administered in a variety of unit dosage forms depending on the method of administration. For example, unit dosage forms suitable for oral administration include solid dosage forms such as powder, tablets, pills, capsules, and dragees, and liquid dosage forms, such as elixirs, syrups, and suspensions. The active ingredients may also be administered parenterally in sterile liquid dosage forms. Gelatin capsules contain the active ingredient and as inactive ingredients powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The compositions of the invention may also be administered via liposomes. Liposomes include emulsions, foams, micelles, insoluble monolayers, liquid crystals, phospholipid dispersions, lamellar layers and the like. In these preparations the composition of the invention to be delivered is incorporated as part of a liposome, alone or in conjunction with a molecule which binds to a desired target, such as antibody, or with other therapeutic or immunogenic compositions. Thus, liposomes either filled or decorated with a desired composition of the invention of the invention can delivered systemically, or can be directed to a tissue of interest, where the liposomes then deliver the selected therapeutic/immunogenic peptide compositions.

Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. Ann. Rev. Biophys. Bioeng, 9: 467 (1980), U.S. Pat. Nos. 4,235,871, 4,501,728, 4,837,028, and 5,019,369, incorporated herein by reference.

A liposome suspension containing a composition of the invention may be administered intravenously, locally, topically, etc. in a dose which varies according to, inter alia, the manner of administration, the composition of the invention being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more compositions of the invention of the invention, and more preferably at a concentration of 25%–75%.

For aerosol administration, the compositions of the invention are preferably supplied in finely divided form along with a surfactant and propellant. Typical percentages of compositions of the invention are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

The compositions of the invention can additionally be delivered in a depot-type system, an encapsulated form, or an implant by techniques well-known in the art. Similarly, the compositions can be delivered via a pump to a tissue of interest.

The compositions of the invention are typically administered to patients after the onset of symptoms, although treatment can also be prophylactic in some embodiments. Typically, treatment with direct administration of polypeptides is done daily, weekly, or monthly, for a period of time sufficient to reduce, prevent, or ameliorate symptoms. Treatment with the nucleic acids of the invention is typically done at intervals of several months. In some embodiments, administration of the compositions of the invention is done in utero.

IX. Gene Therapy

Gene therapy utilizing recombinant DNA technology to deliver nucleic acids encoding HCdc5 polypeptides, or antagonists or agonists of hCdc5 into patient cells or vectors which will supply the patient with gene product in vivo is also contemplated within the scope of the present invention.

Gene therapy techniques have the potential for limiting the exposure of a subject to a gene product, such as a hCdc5 polypeptide, by targeting the expression of the therapeutic gene to a tissue of interest, such as skeletal muscle, myocardium, vascular endothelium or smooth muscle, or solid or circulating tumor cells. For example, WIPO Patent Application Publication No. WO 93/15609 discloses the delivery of interferon genes to vascular tissue by administration of such genes to areas of vessel wall injury using a catheter system. In another example, an adenoviral vector encoding a protein capable of enzymatically converting a prodrug, a "suicide gene", and a gene encoding a cytokine are administered directly into a solid tumor.

Other methods of targeting therapeutic genes to tissues of interest include the three general categories of transductional targeting, positional targeting, and transcriptional targeting (for a review, see, e.g., Miller et al. *FASEB J.* 9: 190–199 (1995)). Transductional targeting refers to the selective entry into specific cells, achieved primarily by selection of a receptor ligand. Positional targeting within the genome refers to integration into desirable loci, such as active regions of chromatin, or through homologous recombination with an endogenous nucleotide sequence such as a target gene. Transcriptional targeting refers to selective expression attained by the incorporation of transcriptional promoters with highly specific regulation of gene expression tailored to the cells of interest.

Examples of tissue-specific promoters include a liver-specific promoter (Zou et al. *Endocrinology* 138: 1771–1774 (1997)); a small intestine-specific promoter (Olivera et al. *J. Biol. Chem.* 271: 31831–31838 (1996)); the promoter for creatine kinase, which has been used to direct the expression of dystrophin cDNA expression in muscle and cardiac tissue (Cox et al. *Nature* 364: 725–729 (1993)); and immunoglobulin heavy or light chain promoters for the expression of suicide genes in B cells (Maxwell et al. *Cancer Res.* 51: 4299–4304 (1991)). An endothelial cell-specific regulatory region has also been characterized (Jahroudi et al. *Mol. Cell. Biol.* 14: 999–1008 (1994)). Amphotrophic retroviral vectors have been constructed carrying a herpes simplex virus thymidine kinase gene under the control of either the albumin or alpha-fetoprotein promoters (Huber et al. *Proc. Natl. Acad. Sci. U.S.A.* 88: 8039–8043 (1991)) to target cells of liver lineage and hepatoma cells, respectively. Such tissue specific promoters can be used in retroviral vectors (Hartzoglou et al. *J. Biol. Chem.* 265: 17285–17293 (1990)) and adenovirus vectors (Friedman et al. *Mol. Cell. Biol.* 6: 3791–3797 (1986)) and still retain their tissue specificity.

Other elements aiding specificity of expression in a tissue of interest can include secretion leader sequences, enhancers, nuclear localization signals, endosmolytic peptides, etc. Preferably, these elements are derived from the tissue of interest to aid specificity.

Viral vector systems useful in the practice of the instant invention include but are not limited to adenovirus, herpesvirus, adeno-associated virus, minute virus of mice (MVM), HIV, sindbis virus, and retroviruses such as Rous sarcoma virus, and MoMLV. Typically, the nucleic acid encoding the therapeutic polypeptide of interest is inserted into such vectors to allow packaging of the nucleic acid, typically with accompanying viral DNA, infection of a sensitive host cell, and expression of the polypeptide of interest.

In still other embodiments of the invention, nucleic acid encoding a therapeutic polypeptide of interest is conjugated to a cell receptor ligand for facilitated uptake (e.g., invagination of coated pits and internalization of the endosome) through a DNA linking moiety (Wu et al. *J. Biol. Chem.* 263: 14621–14624 (1988); WO 92/06180). For example, the DNA constructs of the invention can be linked through a polylysine moiety to asialo-oromucoid, which is a ligand for the asialoglycoprotein receptor of hepatocytes.

Similarly, viral envelopes used for packaging the recombinant constructs of the invention can be modified by the addition of receptor ligands or antibodies specific for a receptor to permit receptor-mediated endocytosis into specific cells (e.g., WO 93/20221, WO 93/14188; WO 94/06923). In some embodiments of the invention, the DNA constructs of the invention are linked to viral proteins, such as adenovirus particles, to facilitate endocytosis (Curiel et al. *Proc. Natl. Acad. Sci. U.S.A.* 88: 8850–8854 (1991)). In other embodiments, molecular conjugates of the instant invention can include microtubule inhibitors (wo/9406922); synthetic peptides mimicking influenza virus hemagglutinin (Plank et al. *J. Biol. Chem.* 269: 12918–12924 (1994)); and nuclear localization signals such as SV40 T antigen (W093/19768).

The nucleic acid can be introduced into the tissue of interest in vivo or ex vivo by a variety of methods. In some embodiments of the invention, the nucleic acid is introduced to cells by such methods as microinjection, calcium phosphate precipitation, liposome fusion, or biolistics. In further embodiments, the nucleic acid is taken up directly by the tissue of interest. In other embodiments, nucleic acid is packaged into a viral vector system to facilitate introduction into cells.

In some embodiments of the invention, the compositions of the invention are administered ex vivo to cells or tissues explanted from a patient, then returned to the patient. Examples of ex vivo administration of gene therapy constructs include Arteaga et al. *Cancer Research* 56 (5): 1098–1103 (1996); Nolta et al. *Proc Natl. Acad. Sci. USA* 93 (6): 2414–9 (1996); Koc et al. *Seminars in Oncology* 23 (1): 46–65 (1996); Raper et al. *Annals of Surgery* 223 (2): 116–26 (1996); Dalesandro et al. *J. Thorac. Cardi. Sur.* 11 (2): 416–22 (1996); and Makarov et al. *Proc. Natl. Acad. Sci. USA* 93 (1): 402–6 (1996).

The following examples are provided to illustrate the invention but not to limit its scope. Other variants of the invention will be readily apparent to one of ordinary skill in the art and are encompassed by the appended claims.

EXPERIMENTAL EXAMPLES

I. Identification and Cloning of the hCdc5 Gene

A. Cloning, Sequencing, and Site-directed Mutagenesis

A novel 1.45-kb cDNA, clone 67, was isolated during a yeast two-hybrid screen of a HeLa cDNA library in pGADGH (Hannon, G. et al., *Genes Dev.* 7: 2378–2391 (1993)) provided by R. Derynck, University of California San Francisco) with cytoplasmic domains (amino acids 775–799, 1094–1115, and 1274–1512) of the human thrombin receptor (Vu, T. et al., *Cell* 64: 1057–1068 (1991)) in the GAL4 binding domain vector, pAS1-CYH (Durfee, T. et al., *Genes Devel.* 7: 555–569 (1993)) (provided by S. Elledge, Baylor College of Medicine). This was sequenced (Sanger, F. et al., *Proc. Natl. Acad. Sci. U.S.A.* 74: 5463–5467 1977)) and used to screen a HeLa cDNA library in Uni-ZAP XR (Stratagene) for full-length clones. The 1.45-kb cDNA insert from clone 67 was labeled using the ECL enhanced chemiluminescence system (Amersham Corp.) according to the protocol provided, and plaques were screened using standard techniques (Sambrook, J. et al., *Molecular Cloning: A Laboratory Manual,* 2nd ed., Cold Spring Harbor Laboratory, Cold Spring Harbor, N.Y. (1989)) as modified in the ECL protocol. Eleven Uni-ZAP XR clones were excised in vivo into SK phagemid according to the protocol from Stratagene. The 2.8-kb insert from phagemid clone 67.1 was sequenced (Sanger, F. et al., *Proc. Natl. Acad. Sci. U.S.A.* 74: 5463–5467 (1977)), and identity with pGADGH clone 67 was established. Clone 67.1 was modified after ultimate codon 802 to add an epitope (DYKDDDK, SEQ ID No: 12) recognized by monoclonal antibody M2 (Kodak/IBI) using site-directed mutagenesis (Kunkel, T. A. et al., *Methods Enzymol.* 154: 367–382 (1987). The epitope-tagged insert was then excised from SK at NotI/ApaI restriction sites and subcloned into these same sites in pcDNA3 (Invitrogen) (Sambrook, J. et al., *Molecular Cloning: A Laboratory Manual,* 2nd ed., Cold Spring Harbor Laboratory, Cold Spring Harbor, N.Y. (1989)). This clone, pcD67F, was used in all further studies, as described below.

Related sequences were identified using the basic local alignment search tool (Altschul, S. et al., *J. Mol. Biol.* 215: 403–410 (1990) and sequence data bases available from the National Center for Biotechnology Information. Alignments and Pustell dot matrix homology analyses were performed using MacVector sequence analysis software (Oxford)

B. Northern Analysis

The human multiple tissue Northern blot (Clontech) was prehybridized in 750 mM sodium chloride, 50 mM sodium phosphate, pH 7.4, 5 mM EDTA, 0.2% Ficoll, 0.2% polyvinylpyrrolidone, 0.2% bovine serum albumin, 50% deionized formamide, 2% sodium dodecyl sulfate, 100 µg/ml sheared salmon sperm DNA (Sigma) at 42° C. for 4 h, then hybridized in the same solution containing 1.2×106 cpm/ml labeled probe at 42° C. for 24 h. Following hybridization, the blot was rinsed three times in 300 mM sodium chloride, 30 mM sodium citrate, pH 7, 0.05% sodium dodecyl sulfate at room temperature, then three times in the same solution at room temperature for 10 min. then two times in 15 mM sodium chloride, 1.5 mM sodium citrate, pH 7, 0.1% sodium dodecyl sulfate at 50° C. for 20 min. The washed membrane was exposed to x-ray film for 24 h with one intensifying screen at −70° C. The NotI/ApaI fragment of pcD67F or a human β-actin cDNA control (Clontech) was labeled to a specific activity of 3×10$^8$ cpm/µg using the Prime-It II random primer labeling kit (Stratagene) according to the manufacturer's instructions. The blot was stripped between hybridizations by washing two times in 0.5% sodium dodecyl sulfate at 100° C. for 10 min.

C. Cell Culture and Transfection

COS-7 and CV-1 cell lines were maintained in DMEM H-16 medium with 3 g/liter glucose (Life Technologies, Inc.) and 10% bovine calf serum (Life Technologies, Inc.). Transfections were performed using LipofectAMINE (Life Technologies, Inc.) according to the protocol provided by the manufacturer. Transiently tmansfected cells were allowed to recover in DMEM with serum for 12–18 h. then incubated an additional 18–24 h. in serum-free DMEM containing 0.1% bovine serum albumin. Serum-deprived cells then were stimulated with DMEM with or without 10% bovine calf serum or 0.1% bovine serum albumin.

D. Western Analysis

Cell monolayers were placed on ice and rinsed with cold phosphate-buffered saline with protease/phosphatase inhibitors (100 µg/ml phenylmethylsulfonyl fluoride, 2 µg/ml aprotinin, 1 µg/ml leupeptin, 1 µg/ml soybean trypsin inhibitor, 1 µg/ml pepstatin A, 10 µg/ml benzamidine, 20 µM okadaic acid, 200 µM sodium orthovanadate, 10 mM sodium pyrophosphate). Cells were then scraped into the rinsing buffer and pelleted at 1,500×g at 4° C. Pellets were resuspended in an equal volume of 2×gel loading buffer (100 mM Tris, pH 6.8, 4% sodium dodecyl sulfate, 20% glycerol, 200 mM dithiothreitol, 0.2% bromphenol blue) and sheared by passage through 21- and 27-gauge syringe needles. Samples were analyzed by electrophoresis in 8% polyacrylamide and transferred to nitrocellulose according to standard protocols (Sambrook, J. et al., *Molecular Cloning: A Laboratory Manual,* 2nd ed., Cold Spring Harbor Laboratory, Cold Spring Harbor, N.Y. (1989)).

Membranes were blocked in TNT (50 mM Tris, pH 7.4, 0.5% sodium chloride, 0.05% Tween 20) with 5% non-fat dried milk at room temperature for 30 min., incubated in the same solution with 10 µg/ml M2 antibody at 4° C. for 18 h. washed in TNT, incubated with horseradish peroxidase-conjugated goat anti-mouse antibody (Bio-Rad) at 1:20,000 dilution in TNT, 5% non-fat dried milk at room temperature for 30 min., and washed in TNT. Blots were rinsed in 50 mM Tris, pH 7.4, 0.5% sodium chloride, then developed using ECL according to the manufacturer's instructions.

E. Immunofluorescence Microscopy

COS-7 or CV-1 cells were plated on sterile 4.8-cm$^2$ glass coverslips and transfected as described above. Following transfection and treatment with serum or albumin, cells were fixed at room temperature in 4% paraformaldehyde in phosphate-buffered saline. Coverslips were then rinsed with blocking solution (150 mM sodium acetate, pH 7, 0.1% non-fat dried milk in phosphate-buffered saline), permeabilized with 0.5% Triton X-100 in blocking solution, rinsed with washing solution (15 mM sodium acetate, pH 7, 0.1% non-fat dried milk in phosphate buffered saline), incubated with 10 µg/ml M2 antibody in washing solution, rinsed with washing solution, incubated with 2 µg/ml fluorescein isothiocyanate-conjugated goat anti-mouse antibody (Life Technologies, Inc.) in washing solutions, and rinsed with phosphate-buffered saline, all at room temperature. Coverslips were mounted on slides using Slow Fade Light Antifade (Molecular Probes) and examined using a Nikon Microphot-FXA fluorescence microscope.

F. Labeling of Cells and Immunoprecipitation of hCdc5

COS-7 cells were transiently transfected with pcD67F, serum-deprived, and labeled with [$^{32}$p] orthophosphoric acid (Dupont NEN) according to standard methods (Ausabel, F. et al., *Short Protocols in Molecular Biology*, John Wiley and Sons, New York, pp. 17.3–17.5 (1995)). Following serum stimulation with phosphate-free DMEM (Life Technologies, Inc.) and 10% dialyzed fetal calf serum (Life Technologies, Inc.), cells were placed on ice, scraped into cold phosphate-buffered saline with protease/phosphatase inhibitors, and pelleted at 1,500×g at 4° C. Cell pellets were resuspended in RIPA buffer (10 mM Tris, pH 7.4, 500 mM NaCl, 1 mM EDTA, 1% Triton X-100, 1% sodium deoxycholate, 0.5% sodium dodecyl sulfate) with protease/phosphatase inhibitors and sheared by passage through 21- and 27-gauge syringe needles. Cell lysates were extracted for 60 min at 4° C. and then centrifuged at 15,000×g for 15 min. at 4° C. Supernatants were precleared with protein A-Sepharose (Pharmacia Biotech Inc.) for 60 min. at 4° C. and then incubated with 10 µg/ml M2 antibody for 3 h. at 4° C. Protein A-Sepharose was added, and incubations were continued for 60 min. Immunoprecipitates were washed with RIPA buffer and then suspended in gel loading buffer and boiled prior to electrophoresis in 8% polyacrylamide. Dried gels were exposed to x-ray film with two intensifying screens for 4–72 h. at −70° C.

Densitometric analysis was accomplished by scanning representative autoradiographs into Photoshop (Adobe), then measuring signal densities using NIH Image (NIH). Signal densities were normalized against chemiluminescence signals obtained from Western blots of similarly treated, unlabeled samples.

G. Results and Discussion

The 1.45-kb partial cDNA identified during the yeast two-hybrid screen contained an open reading frame encoding a potential DNA binding domain. This cDNA was used to isolate a 2.85-kb cDNA from a HeLa cell cDNA library which contained a complete open reading frame encoding an 802-amino acid protein (FIG. 1A (SEQ ID NO: 1)). The protein sequence contained two tandem repeats of a helix-turn-helix DNA binding motif (Nelson, H. C. M., *Curr. Opin. Genet. Dev.* 5: 180–189 (1995)), four consensus nuclear localization signals (Boulikas, T., *Crit. Rev. Eukaryot. Gene Expr.* 3: 193–227 (1993)), a proline-rich, hydrophilic region similar to known activating domains (Mitchell, P. J. et al., *Science* 245: 371–378 (1989); Tijan, R. et al., *Cell* 77: 5–8 (1994)), and potential sites for phosphorylation by intracellular kinases (FIGS. 1, A and B).

Figure 2A:
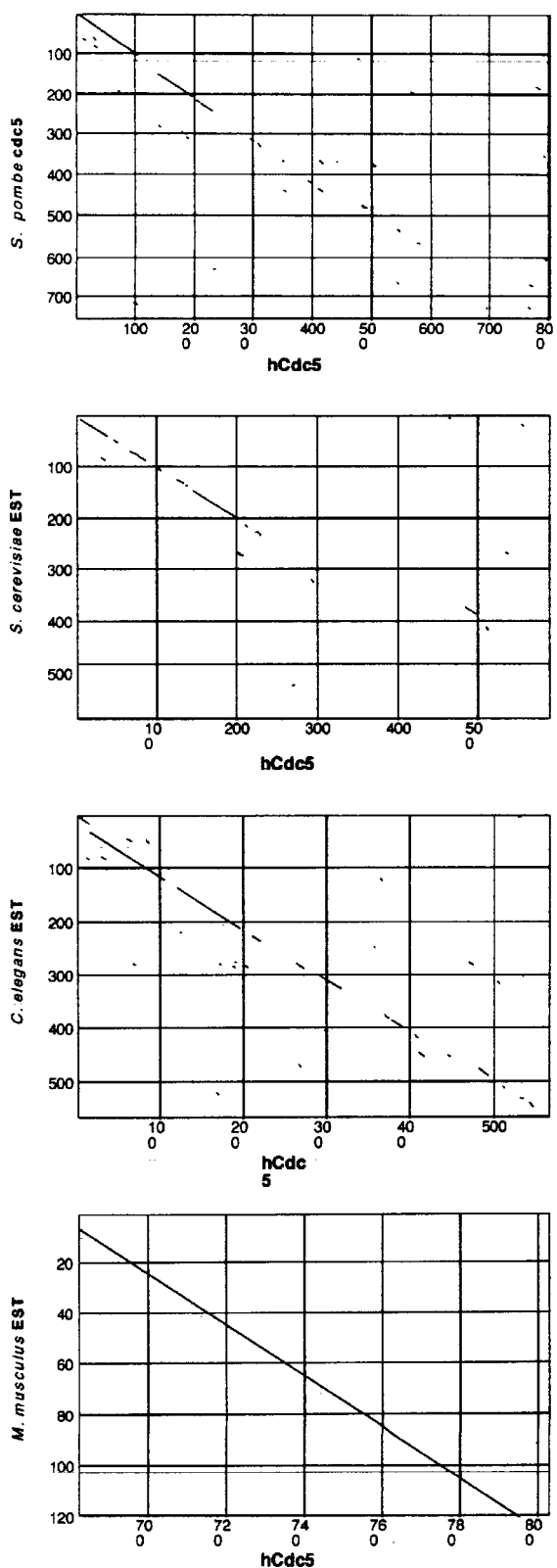
FIG. 2A depicts dot matrix plots demonstrating homology with *S. pombe* Cdc5 as well as expressed sequence tags in *M. musculus, C. elegans,* and *S. cerevisiae*. Contiguous amino acids, as indicated by coordinates, were aligned using a Pustell homology matrix with window size=8, minimum percent score=60, and hash value=2.

A search for related cDNA sequences revealed significant homology with the cdc5 gene product in *S. pombe* (Ohi, R. et al., *EMBO J.* 13: 471–483 (1994)). The two proteins were 75% identical over the 223 amino acids comprising the DNA binding and nuclear localization domains and 17% identical over the subsequent 535 amino acids (FIG. 2A). Amino acids 4–56 and 57–107 of hCdc5 represent two tandem repeats of a helix-turn-helix motif similar to the DNA binding domain of Myb-related proteins (FIG. 2B). This region was 83% identical to the analogous region (amino acids 2–103) of S. pombe Cdc5 (SEQ ID No: 3) (Ohi, R. et al., EMBO J. 13: 471–483 (1994)) and 36–38% identical to the corresponding domains in the human Myb subfamilies (SEQ ID No: 4–6) (Majello, B. et al., Proc. Natl. Acad. Sci. U.S.A. 83: 9636–9640 (1986); Nomura, N. et al., Nucl. Acids Res. 16: 11075–11089 (1988)). Carboxyl to this region was a hydrophilic stretch of 223 residues (amino acids 378–500, SEQ ID No: 7), with some homology to the activating domains of a- and b-Myb (SEQ ID No: 10 and 9) (Majello, B. et al., Proc. Natl. Acad. Sci. U.S.A. 83: 9636–9640 (1986); Nomura, N. et al., Nucl. Acids Res. 16: 11075–11089 (1988) and S. pombe Cdc5 (SEQ ID No: 8) (Ohi, R. et al., EMBO J. 13: 471–483 (1994)) (FIG. 2C). This analysis indicates that hCdc5 and S. pombe Cdc5 are related proteins, with significant similarity to the Myb family.

A search of expressed sequences revealed that homologous open reading frames are present in M. musculus (GenBank Accession no. W82296), C. elegans (Wilson, R. et al., Nature 368: 32–38 (1994)), and S. cerevisiae (GenBank Accession no. Z49809) (FIG. 2A). The murine expressed sequence tag aligns with the carboxyl terminus of hCdc5 and is 97% identical over the 127 amino acids available, suggesting that this is almost certainly the murine homolog of hCdc5. The 528-amino acid polypeptide encoded by a C. elegans gene is 80% identical over the first 205 residues, including the DNA binding domain and nuclear localization signals of hCdc5, and 30% identical over the remaining 323 amino acids. An open reading frame in S. cerevisiae reveals 54% identity over the first 230 residues and 14% identity over the remaining 332 amino acids. The finding of open reading frames encoding proteins with similar domain arrangements and amino acid sequences in human, mouse, nematode, and budding and fission yeast indicates that hCdc5 is a member of a protein family that has been highly conserved throughout evolution.

Figure 3:
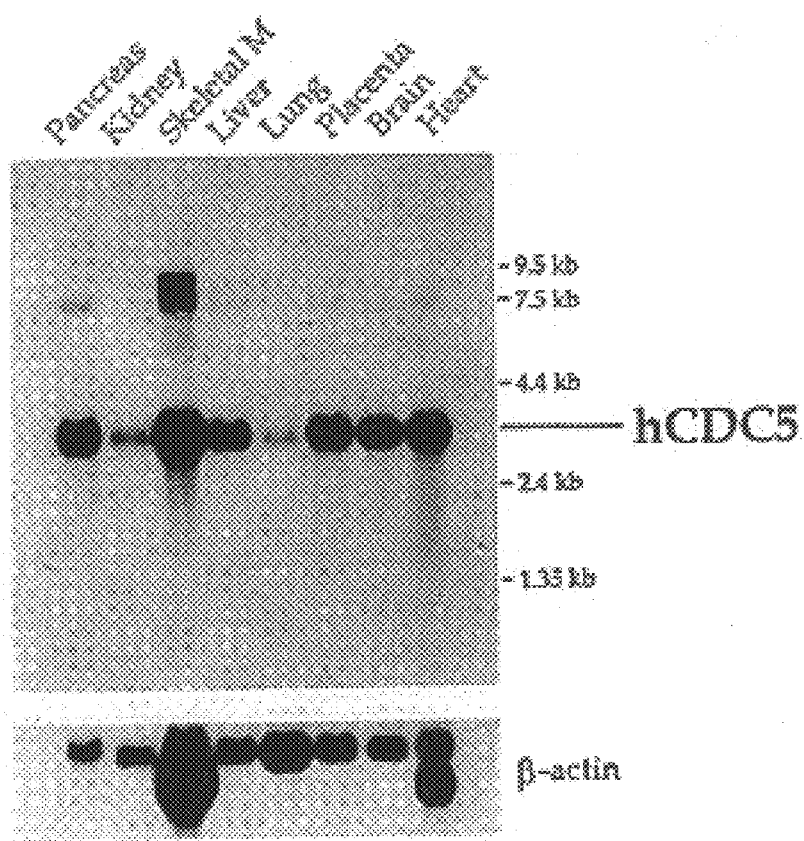
FIG. 3 is a Northern blot of poly(A) mRNA probed with a 2.85-kb cDNA for hCdc5 (top) and with cDNA for β-actin as a control for the amount of mRNA loaded in each lane (bottom).

Northern analysis at high stringency revealed a dominant band at 3.4 kb in all human tissues examined (FIG. 3). In skeletal muscle, heart, pancreas, and placenta, a less prominent 8–9 kb band was observed. How this larger mRNA species related to the dominant 3.4-kb species remains to be determined. Of note, the wide expression of hCdc5 in normal adult human tissues contrasts with c-Myb, which is expressed almost exclusively in hematopoietic cells (Luscher, B. et al., Genes Dev. 4: 2235–2241 (1990); Thompson, M. A. et al., Bioassays 17: 341–350 (1995)). These findings suggest that hCdc5 may serve a more general function in transcriptional regulation.

To determine its location in mammalian cells, an epitope-tagged version of hCdc5 was transiently expressed in CV-1 cells. Cells grown in standard culture medium with 10% bovine calf serum demonstrated nuclear localization of hCdc5, consistent with a role in transcriptional regulation. Remarkably, however, hCdc5 was found exclusively in the cytoplasm in transfected CV-1 cells deprived of serum. When these serum deprived cells were then stimulated with 10% bovine calf serum for 5, 15, or 60 min., hCdc5 was found solely in the nucleus. This same phenomenon was observed in transiently transfected COS-7 cells. To the extent that the results obtained with epitope-tagged hCdc5 expressed in CV-1 or COS-7 cells accurately reflect the behavior of endogenous hCdc5, the rapid nuclear translocation of hCdc5 in response to serum stimulation suggests a role in relaying signals from the cell surface to the nucleus.

Figure 4A:
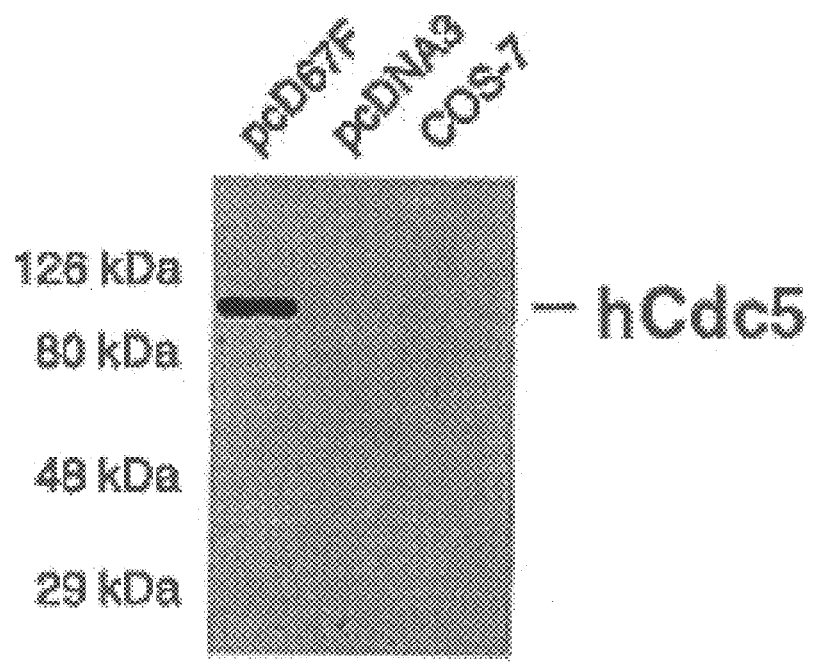
FIG. 4A is a Western blot using M2 monoclonal antibody to detect epitope-tagged hCdc5 in transfected COS-7 cells (COS-7, untransfected cells; pcDNA3, expression vector only; pcD67F, vector directing HCdc5 expression) The 105-kDa transfection-dependent band is designated hCdc5.

Many transcription factors contain phosphorylation sites that regulate nuclear localization as well as DNA binding and transactivation (Vandromme, M. et al., Trends Biochem. Sci. 21: 59–64 (1996)). hCdc5 contains 28 potential phosphorylation sites: 14 for recognition by casein kinase II (S/T-X-X-D/E), 9 for protein kinase C (S/T-X-R/K), 2 for protein kinase A (R/K-X-X-S/T), and 3 for MAP kinase (P-X-S/T-P or P-X-X-S/T-P) (see FIG. 1). Western blot analysis of whole cell lysates from COS-7 cells expressing epitope-tagged hCdc5 demonstrated a single, transfection-dependent band at about 105 kDa (FIG. 4A). This is greater than the predicted size of 92.2 kDa, suggesting the possibility that hCdc5 either maintains a structure that slows its mobility on gel electrophoresis or carries post-translational modifications.

Figure 4B:
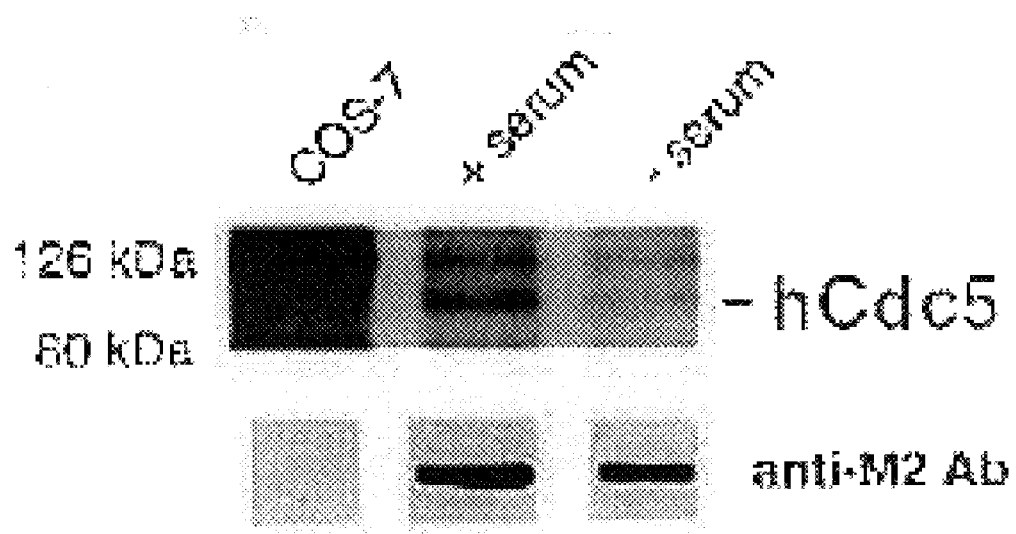
FIG. 4B depicts an autoradiograph of hCdc5 immunoprecipitates resolved by sodium dodecyl sulfate-polyacrylamide gel electrophoresis (top). The transfection-dependent band at 105 kDa is designated hCdc5. In the lower panel the immunoprecipitates were resolved by gel electrophoresis and analyzed using M2 monoclonal antibody (bottom).

To test the hypothesis that hCdc5 is a phosphoprotein, immunoprecipitates of $^{32}$P-labeled COS-7 cells expressing epitope-tagged hCdc5 were analyzed by sodium dodecyl sulfate-polyacrylamide gel electrophoresis. Autoradiography revealed a transfection-dependent, $^{32}$P-labeled band of the appropriate molecular weight (FIG. 4B). The intensity of this band doubled within 10 min. of serum stimulation, as quantitated by densitometry. Thus, although recombinant hCdc5 was phosphorylated in non-stimulated COS-7 cells, the degree of phosphorylation or the amount of phosphoprotein available for immunoprecipitation increased with serum stimulation.

Precedent for phosphorylation-dependent translocation of transcription factors is well established (Vandromme, M. et al., Trends Biochem. Sci. 21: 59–64 (1996)). Several potential phosphorylation sites flank the four consensus nuclear localization signals in hCdc5 (FIG. 1A). In addition, these nuclear localization signals and phosphorylation sites are conserved in S. pombe Cdc5. Whether phosphorylation regulates translocation, DNA binding, or activation for these putative transcription factors remains to be determined.

The relatedness of hCdc5 to S. pombe Cdc5 prompts speculation about its possible function. The S. pombe molecule has been implicated in the regulation of cell division, specifically at the G2/M transition (Nasmyth, K. et al., Mol. Gen. Genet. 182: 119–124 (1981); Ohi, R. et al., EMBO J. 13: 471–483 (1994)). hCdc5 is almost certainly a serum-regulated transcription factor. Taken together with its similarity to S. pombe Cdc5 and its ubiquitous expression, this suggests a possible role for hCdc5 in cell cycle control.

Similarities and differences between hCdc5 and c-Myb also are worthy of comment. The DNA binding ability of the helix-turn-helix motif seen in hCdc5 has been well characterized (Nelson, H. C., Cur. Opin. Genet. Dev. 5: 180–189 (1995)). In contrast with the DNA binding domain seen in Myb, both hCdc5 and S. pombe Cdc5 contain only two tandem repeats of the helix-turn-helix motif, whereas Myb family members possess three. Moreover, within this domain both hCdc5 and S. pombe Cdc5 bear a valine to leucine substitution at a position critical for DNA binding specificity (Ogata, K. et al., Nat. Struct. Biol. 3: 187–187 (1996); Carr, M. D. et al., Eur. J. Biochem 235: 721–735 (1996)). hCdc5 and S. pombe Cdc5, therefore, may differ from Myb in their DNA binding properties. As noted above, the expression pattern of hCdc5 differs from that of the Myb family. These observations suggest that although hCdc5 and S. pombe Cdc5 share similarity with the Myb family, they are likely to have distinct biological roles.

II. Function of hCdc5

A. Cell Culture

All cell lines were obtained from the American Type Culture Collection. BALBc/3T3 and COS-7 cell lines were maintained in Dulbecco's Modified Eagle's media made 10% bovine calf serum (Life Technologies). Jurkat cells were maintained in RPMI 1640 media made 10% feta bovine serum (Life Technologies). Cells were detached for passage and cell growth assays using 0.05% trypsin, 0.02% EDTA in 0.9% NaCl. Synchronization of BALBc/3T3-derived cultures in G0 was accomplished by washing cells with serum-free media and maintaining in media made 0.5% bovine calf serum for 48 hours. Release into G1 was accomplished by the addition of pre-warmed bovine calf serum to 10%.

B. Mammalian Expression Constructs

Plasmid 67F, encoding FLAG-tagged, full-length hCdc5 in pcDNA3 was constructed as previously described (Bernstein, H. S. et al., *J. Biol. Chem.* 272: 5833–5837 (1997)). pUHD 15-1, which directs the expression of a fusion of the bacterial tetracycline repressor DNA binding domain with the *H. simplex* virion protein 16 activating domain, was obtained from Display Systems Biotechnology. pUH67F, encoding epitope-tagged hCdc5 3' to seven tandem copies of the tet operator and a minimal CMV promoter, was constructed by subcloning an ApaI/KspI fragment from pSK67F (Bernstein, H. S. et al., *J. Biol. Chem.* 272: 5833–5837 (1997)) into the XbaI/KspI sites of pUHD 10-1 (Display Systems Biotechnology) after filling in ApaI and XbaI ends with T4 DNA polymerase. pNGFP-N1, encoding green fluorescent protein with F64L and S65T mutations, was obtained from Clontech and used as a marker for transfection, (Iavarone, A. et al., *Nature* 387: 417–422 (1997)).

C. Transfection and Generation of Stable Cell Lines

COS-7 and BALBc/3T3 cells were transfected using LipefectAMINE (Life Technologies) according to the manufacturer's instructions. Cell line 3T15.8 was generated by transfecting plasmid pUHD 15-1 into BALBc/3T3 cells and selecting clones in the presence of 400 $\mu$g/ml G418 (Geneticin; Life Technologies). Clones were then tested for their ability to induce expression from the tet operative-CMV promoter in transient transfection assays using a luciferase reporter plasmid, pUHC 13-3 (Display Systems Biotechnology). pUHC 13-3 was transfected into G418-resistant clones in the presence or absence of 10 $\mu$g/ml tetracycline (Sigma). Cells were assayed for luciferase activity using the Luciferase Assay System (Promega) according to the manufacturer's protocol. Clone 3T15.8 was found to induce expression of luciferase activity in the absence of tetracycline with barely detectable activity in the presence of tetracycline and was chosen for use in subsequent experiments. This cell line was maintained in 400 $\mu$g/ml G418 and 10 $\mu$g/ml tetracycline.

To generate a stable cell line expressing an epitope-tagged hCdc5 (Bernstein, H. S. et al., *J. Biol. Chem.* 272: 5833–5837 (1997)) under control of the tet operator, plasmid pUH67F was transfected into cell line 3T15.8 together with plasmid CA10 (obtained from D. O. Morgan, UCSF), which provided a marker for hygromycin resistance. Tetracycline was added to the culture media and clones were selected with 200 $\mu$g/ml hygromycin (Boehringer Mannheim). Clones were screened for their ability to express hCdc5 in the absence of tetracycline by immunoblot analysis as described below. Clone 3T15.8.22 showed increased expression detectable by immunoblot in the presence of tetracycline and was selected for use in the experiments described. This cell line was maintained in 400 $\mu$g/ml G418, 200 $\mu$g/ml hygromycin, and 10 $\mu$g/ml tetracycline.

To assess the effects of constitutive hCdc5 overexpression, tetracycline was removed from cultures by rinsing adherent cells with media without tetracycline, and re-feeding with fresh media every 2 hours for 6 hours. Maximal expression of exogenous hCdc5 was reached by 36 hours after tetracycline removal (FIG. 5), thus experiments were designed to allow cells 36–48 hours under tetracycline-free conditions before assaying effects of hCdc5 overexpression.

Transient transfection of Jurkat cells was accomplished by electroporation. Briefly, about $10^7$ cells in media with serum were placed on ice and mixed with a total of 20 $\mu$g plasmid DNA. Electroporation was performed with a Gene Pulser (Bio-Rad) set at 250 mV, 960 $\mu$F. Cells were immediately inoculated into 10 ml media with serum and incubated at 37° C. under 5% $CO_2$ for 24 hours, then expanded to 20 ml and incubated an additional 72 hours before analysis.

D. Antibody Production and Immunoblot Analysis

A peptide representing the carboxyl terminus of hCdc5 (SEQ ID No: 1, amino acids 769–788) was synthesized at the Biomolecular Resource Center, University of California, San Francisco and conjugated to keyhole limpet hemocyanin using an ImJect Activated Immunogen Conjugation kit (Pierce) according to the manufacturer's instructions. Immunizations and fusions were performed essentially as described (Harlow, E. et al., *Antibodies: A Laboratory Manual* Cold Spring Harbor, N.Y. 1988)). Ten days post fusion, hybridoma supernatants were screened for antibodies against the peptide by ELISA. Hyridomas producing antibodies of interest were subcloned and expanded. Subclones were tested in immunoblot assays using hybridoma supernatant preabsorbed with peptide as a negative control. Clone B1 was used for subsequent experiments. Rabbit polyclonal antisera raised against the KLH-conjugated peptide were produced by Animal Pharm Services (Healdsburg). Monoclonal antibody M2 directed against the FLAG epitope was obtained from Kodak. Polyclonal antibodies cross-reactive against mouse and human cyclins E, A, and B1 were obtained from Santa Cruz Biotechnology.

Immunoblot analysis was performed essentially as described Bernstein, H. S. et al., *J. Biol. Chem.* 272: 5833–5837 (1997)). Briefly, cell monolayers were scraped into cold phosphate buffered saline and pelleted at 1500×g at 4° C. Pellets were resuspended in an equal volume of 2×gel loading buffer (100 mM Tris, pH 6.8, 4% sodium dodecyl sulfate, 20% glycerol, 200 mM dithiothreitol, 0.2% bromophenol blue) and sheared by passage through 21- then 27-gauge syringe needles. Samples were analyzed by electrophoresis in 8% or 10% polyacrylamide and transferred to nitrocellulose according to standard protocols. Membranes were blocked in TNT (50 mM Tris, pH 7.4, 0.5% sodium chloride, 0.05% Tween-20) made 5% non-fat dried milk at room temperature for 30 min., and incubated in the same solution made either 10 $\mu$g/ml monoclonal antibody, 1:100 dilution with hyridoma supernatant, or 3 $\mu$g/ml polyclonal antibody at 4° C. for 1–3 hours. Blots were then washed in TNT, incubated with horseradish peroxidase (HRP)-conjugated goat anti-mouse antibody (Bio-Rad) at 1:10,000 dilution or HRP-conjugated goat anti-rabbit antibody (Bio-Rad) at 1:5,000 dilution in TNT-5% non-fat dried milk at room temperature for 30 min. and washed in TNT. Blots were rinsed in 50 mM Tris, pH 7.4, 0.5% sodium chloride, then developed using the ECL enhanced chemiluminescence system (Amersham) according to the manufacturer's instructions. Densitometric analysis was accomplished by scanning representative ECL results into Photoshop (Adobe), then measuring signal densities using NIH Image (NIH).

E. Immunofluorescence

Immunofluorescence analysis was performed essentially as described (Bernstein, H. S. et al., *J. Biol. Chem.* 272: 5833–5837 (1997)). BALBc/3T3 or 3T15.8.22 cells were plated on sterile 4.8 cm$^2$ glass coverslips in low serum and stimulated with 10% bovine calf serum for 10 min. Cells were then placed on ice and fixed at room temperature in 4% paraformaldehyde in phosphate-buffered saline. Cover slips were washed with quenching solution (150 mM sodium acetate, pH 7, 0.1% non-fat dried milk in phosphate-buffered saline), permeabilized with 0.5% triton X-100 in quenching solution, washed with washing solution (15 mM sodium acetate, pH 7, 0.1% non-fat dried milk in phosphate-buffered saline), incubated with either 10 μg/ml monoclonal antibody or 1:10 dilution of polyclonal antiserum in washing solution, washed with washing solution, incubated with 2 μg/ml fluorescein isothiocyanate-conjugated goat anti-mouse antibody (Life Technologies) or 5 μg/ml Texas red-conjugated goat anti-rabbit antibody (Molecular Probes) in washing solution, and washed with phosphate-buffered saline, all at room temperature. Cover slips were mounted on slides using Slow Fade Anti-Fade (Molecular Probes) and examined using a Nikon Microphot-FXA fluorescence microscope.

F. Cell Cycle Analysis

For cell cycle distribution analysis of BALBc/3T3 cultures, cells were synchronized as described above, then stimulated with serum and analyzed about 10$^6$ cells at each timepoint were fixed in 95% ethanol, stained with propidium iodide (PI), and analyzed for DNA content using a Becton Dickinson FACScan with an argon ion laser at 488 nm and 250 mW light output. PI emission signals were acquired using 630/22 nm bandpass filter. All analyses of DNA content were performed on 20,000 collected events using CellQuest software (Becton Dickinson), except where indicated. Two-tailed P values were obtained using the Student t test for unpaired data.

For cell cycle distribution analysis of cells overexpressing hCdc5, actively dividing or synchronized 3T15.8.22 or 3T15.8 cells were grown in the presence or absence of tetracycline. Cells were analyzed at indicated timepoints following serum stimulation, or after 72 hours of active division. Briefly, about 2×10$^6$ cells at each timepoint were stained with PI, to identify dead cells, and Hoechst 33342, which provides a measure of DNA content in living cells. Flow cytometry was performed using a Becton Dickinson FACStar Plus with dual argon ion lasers at 488 and 363 nm light output. PI signals were collected as above and Hoechst emission signals were acquired using a 470/10 nm bandpass filter.

For analysis of cell cycle distribution in transiently transfected Jurkat cultures, about 3×10$^6$ cells were stained with PI and Hoechst 33342. PI and Hoechst emission signals were acquired for 10$^5$ events using a flow cytometrytar Plus as above. Of these, about 20,000 GFP-expressing cells were collected using a 530/30 nm bandpass filter and analyzed.

G. Results And Discussion

1. Overexpression of hCdc5 Accelerates G2/M Progression

Figure 5:
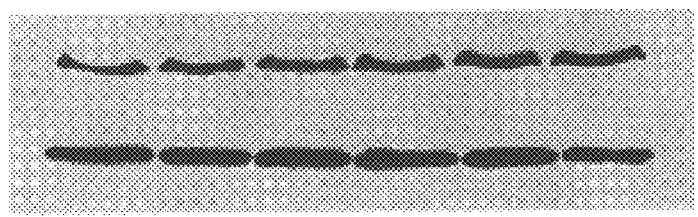
FIG. 5 is an immunoblot of dividing 3T15.8.22 fibroblasts, stably transformed to express hCdc5 under control of the bacterial tetracycline operator, grown in the presence or absence of tetracycline for the times indicated. Whole cell lysates were analyzed by immunoblotting with monoclonal antibodies to either the endogenous protein (B1) or FLAG-epitope present on recombinant hCdc5 (M2). While the recombinant protein is absent from the 3T15.8 parental cell line, it is expressed at levels about 2-fold above the endogenous protein by 36 hours after tetracycline withdrawal, as assessed by densitometry. A non-specific protein (*) recognized by the secondary goat anti-mouse antibody is included as a control to demonstrate the amount of protein loaded in each lane.
Figure 5:
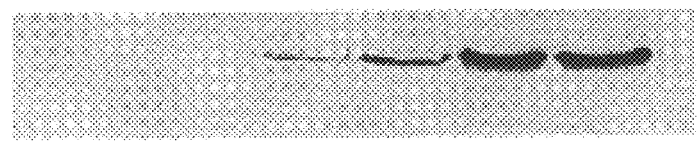

We initially attempted constitutive overexpression of hCdc5 in a variety of cell types but were unable to generate stable lines, suggesting that constitutive expression at high levels was incompatible with cell survival. We therefore generated a BALBc/3T3-based cell line, designated 3T15.8.22, in which hCdc5 was expressed under control of a tetracycline-regulatable promoter (Gossen, M. et al., *Proc. Natl. Acad. Sci. U.S.A.* 89: 5547–5551 (1992); Resnitzky, *Mol. Cell Biol.* 14: 1669–1679 (1994)). Immunoblotting demonstrated that in the absence of tetracycline, recombinant hCdc5 was expressed at levels about 2-fold above that of the endogenous protein (FIG. 5). Like native hCdc5, epitope-tagged recombinant hCdc5 translocated to the nucleus upon serum stimulation.

Figure 6:
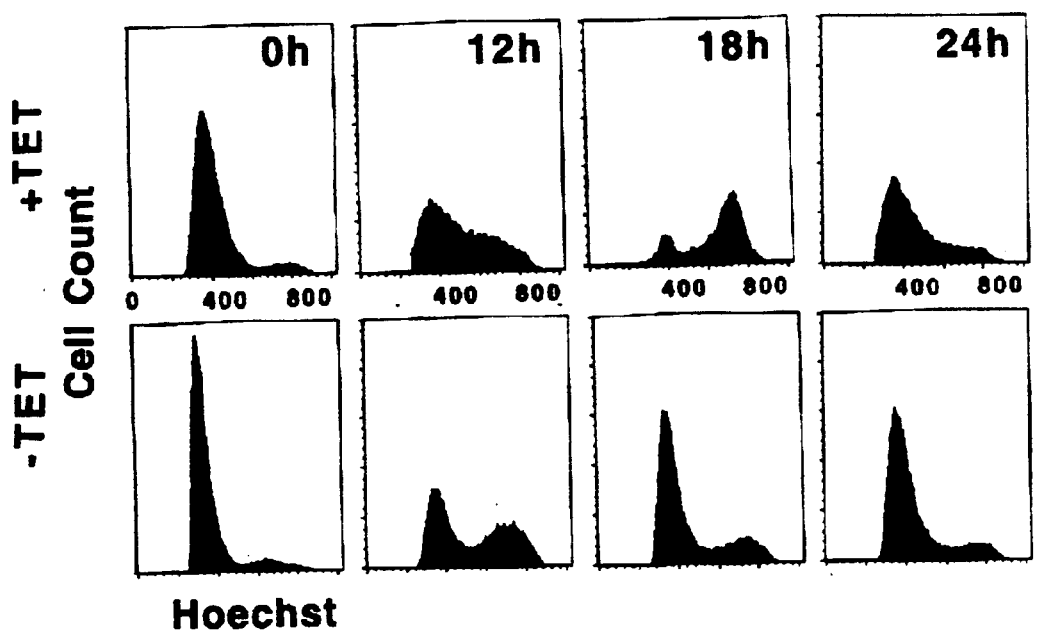
FIG. 6 comprises panels A–H and depicts the results of flow cytometry of 3T15.8.22 cultures synchronized in G0 by growth for 48 hours in media made 0.5% serum with or without tetracycline, released from quiescence by addition of serum to 10%, and analyzed at indicated timepoints. Cells were stained with propidium iodide and Hoechst 33342 to determine viability and DNA content, respectively. The experiment was repeated 5 times, with a representative study shown.
Figure 7:
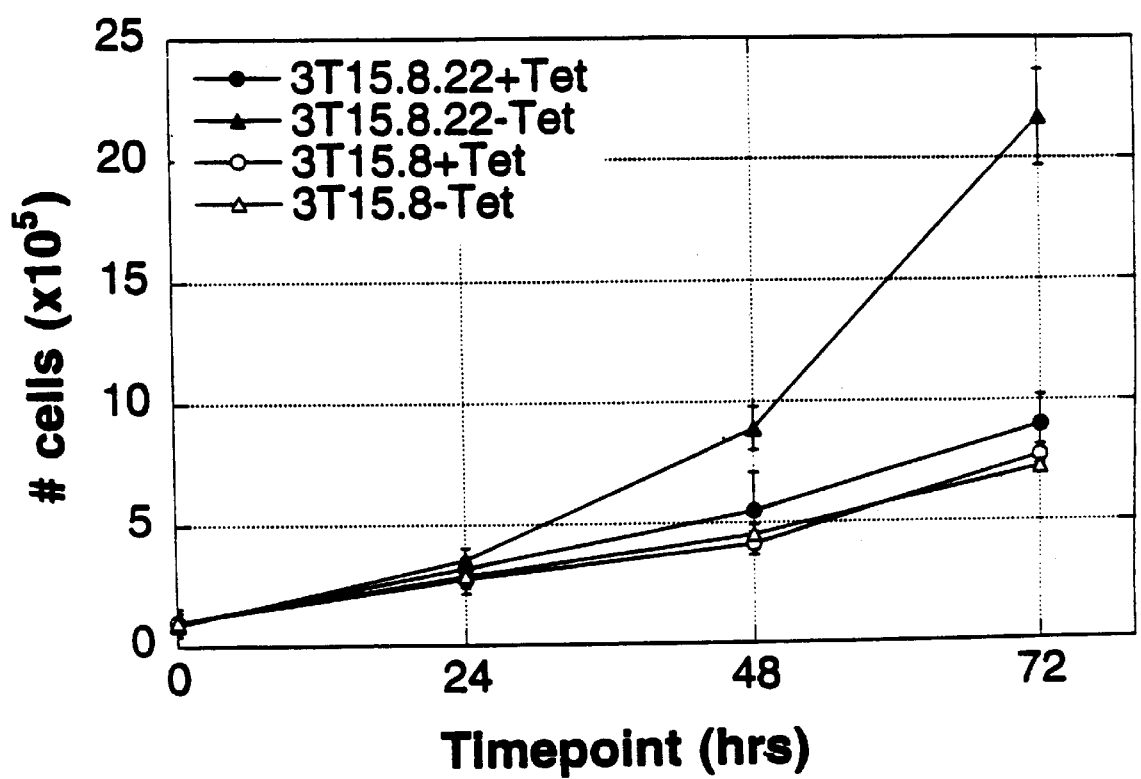
FIG. 7 is a graph depicting actively dividing 3T15.8.22 and parental 3T15.8 parental cultures plated at about 1250 cells/cm2, grown in the presence or absence of tetracycline, and counted at indicated timepoints. Data represent means from 4 experiments+/–sem. Calculated cell cycle lengths are 26 hours for 3T15.8 cultures either in the presence or absence of tetracycline, 28 hours and 19 hours for 3T15.8.22 cultures in the presence or absence of tetracycline, respectively.

In order to assess the effect of increased hCdc5 expression on cell cycle progression, 3T15.8.22 cells were synchronized in G0 with low serum then released in G1 and measured for DNA content as a function of time (FIG. 6, panels A–H). Induction of hCdc5 by removal of tetracycline caused accelerated progression through the cell cycle; cells returned to G1 by 18 hours after release from quiescence in the absence of tetracycline compared with 24 hours in the presence of tetracycline. By contrast, the parent cell line 3T15.8, which expressed the tet repressor-VP16 fusion but not exogenous hCdc5, return to G1 by 24 hours without any tetracycline-dependent effect. This cell cycle acceleration was maintained over time (FIG. 7). Over 72 hours, cells overexpressing hCdc5 exhibited an abbreviated cell cycle length of about 19 hours, while cells in which recombinant hCdc5 expression was repressed by tetracycline grew at a slower rate with a cycle length of about 28 hours. The cell cycle length in 3T15.8 cultures was about 26 hours, unaffected by tetracycline, and similar to that seen in 3T15.8.22 cultures in the presence of tetracycline.

Figure 8:
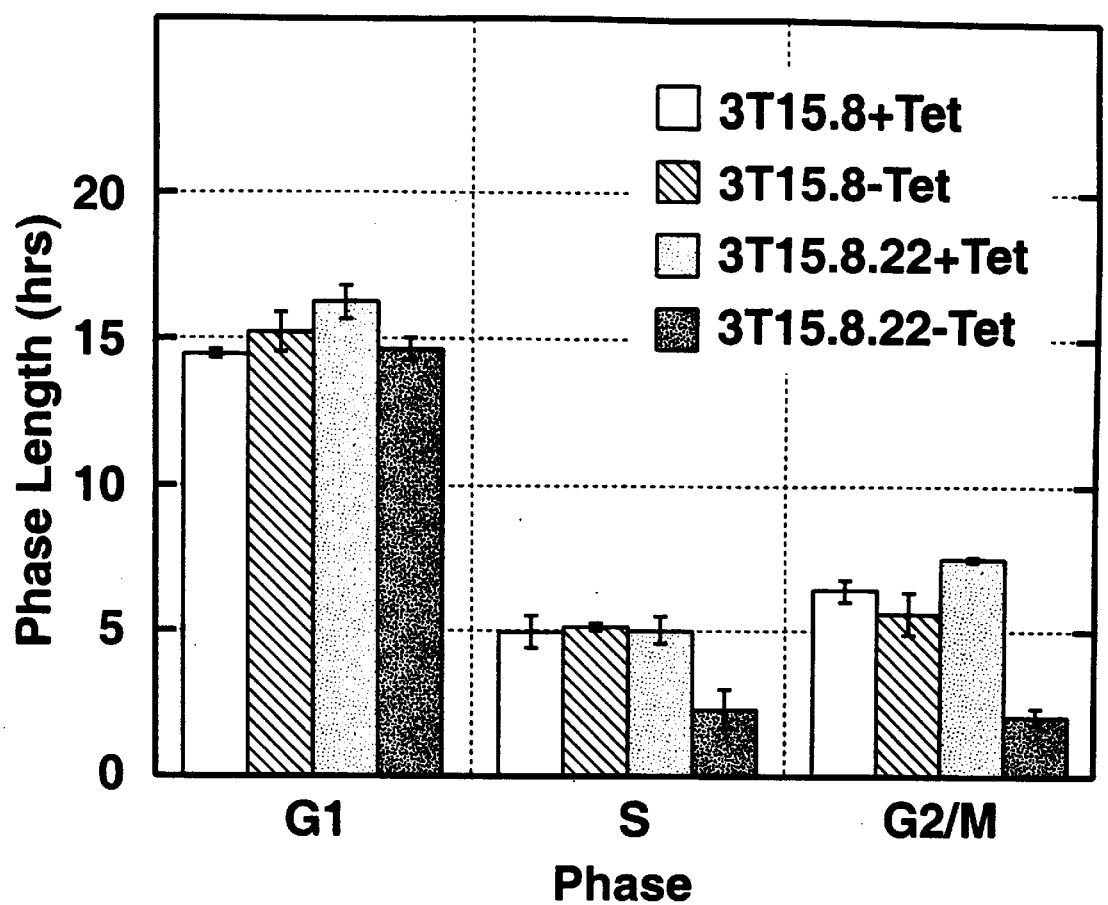
FIG. 8 is a graph depicting alteration of cell cycle distribution in asynchronous cultures resulting from over-expression of hCdc5. Actively dividing 3T15.8.22 and 3T15.8 cultures were grown in the presence or absence of tetracycline for 72 hours, stained with propidium iodide and Hoechst 33342 to determine viability and DNA content, respectively, and analyzed for cell cycle distribution by flow cytometry. Phase lengths were calculated from the percentage of cells in each phase determined by flow cytometry and the cell cycle length calculated from the growth curves in FIG. 7. Data represent means from 4 experiments+/–sem.

To determine which phase of the cell cycle was shortened by overexpression of hCdc5, we analyzed asynchronously dividing 3T15.8.22 and 3T15.8 cultures grown in the presence and absence of tetracycline (FIG. 8). In 3T15.8.22 cultures, a highly significant tetracycline-dependent decrease in the calculated length of G2/M was noted (1.9 h. vs. 7.4 h; p<0.0001). A smaller effect in S phase was also seen (2.2 h. vs. 5 h.; p<0.05). Control 3T15.8 cultures showed no significant tetracycline-dependent effect. Thus, hCdc5 overexpression significantly accelerates G2/M.

2. Overexpression of hCdc5 Overcomes a G2/M Size Checkpoint

Figure 9:
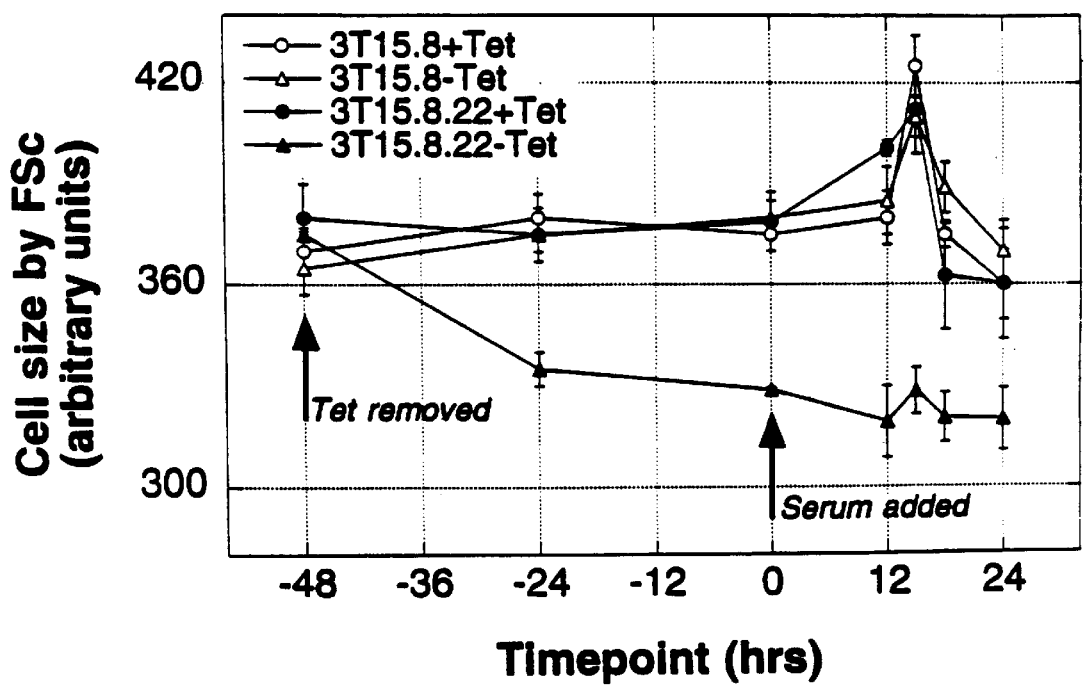
FIG. 9 is a graph depicting the overcoming of a G2/M size checkpoint by overexpression of hCdc5. 3T15.8.22 and 3T15.8 cultures were synchronized in G0, released, and analyzed by flow cytometry as described in FIG. 6. Forward light scatter (Fsc) is plotted as a function of time. Data represent means from 3 experiments+/–sem. Average cell size in serum-deprived cultures overexpressing hCdc5 gradually decreases as cells reach G0. Upon release into G1, 3T15.8.22 cells grown in the absence of tetracycline remain smaller, with no significant increase in size over the course of the cell cycle compared with 3T15.8.22 cells grown in the presence of tetracycline (p=0.05).

In fission yeast, cells must reach a size threshold in order to enter mitosis (Nurse, P., *Nature* 256: 547–551 (1975); Russell, P. et al., *Cell* 49: 559–567 (1987)). Since mammalian cells overexpressing hCdc5 demonstrated an appreciable increase in growth rate and acceleration through G2/M, we asked whether overexpression enabled cells to bypass size requirements for G2 progression and mitotic entry. 3T15.8.22 cultures were synchronized in G0 by serum deprivation in the presence or absence of tetracycline then released into G1 and measured for DNA content and cell size by flow cytometry. In the absence of tetracycline, 3T15.8.22 cultures showed a decrease in average cell size as they completed a division cycle and entered G0. Moreover, unlike the parent cell line or 3T15.8.22 cultures in the presence of tetracycline, they failed to exhibit the expected increase in size as they approached mitosis (FIG. 9). In addition, asynchronously dividing 3T15.8.22 cultures maintained this smaller average cell size in the absence of tetracycline over time. This suggested that overexpression of hCdc5 allowed cells to proceed through G2, bypassing the normal size checkpoint for mitotic entry.

3. Expression of Mutant hCdc5 Delays Mitotic Entry

Figure 10:
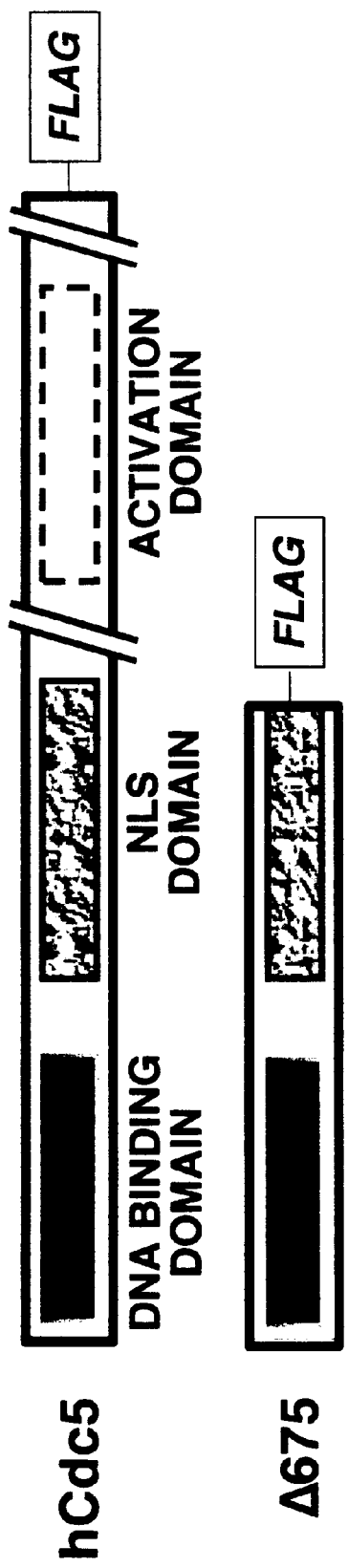
FIG. 10 is a schematic representation of hCdc5 protein indicating the wild-type (hCdc5) and deletion mutant (Δ675) tested.
Figure 11:
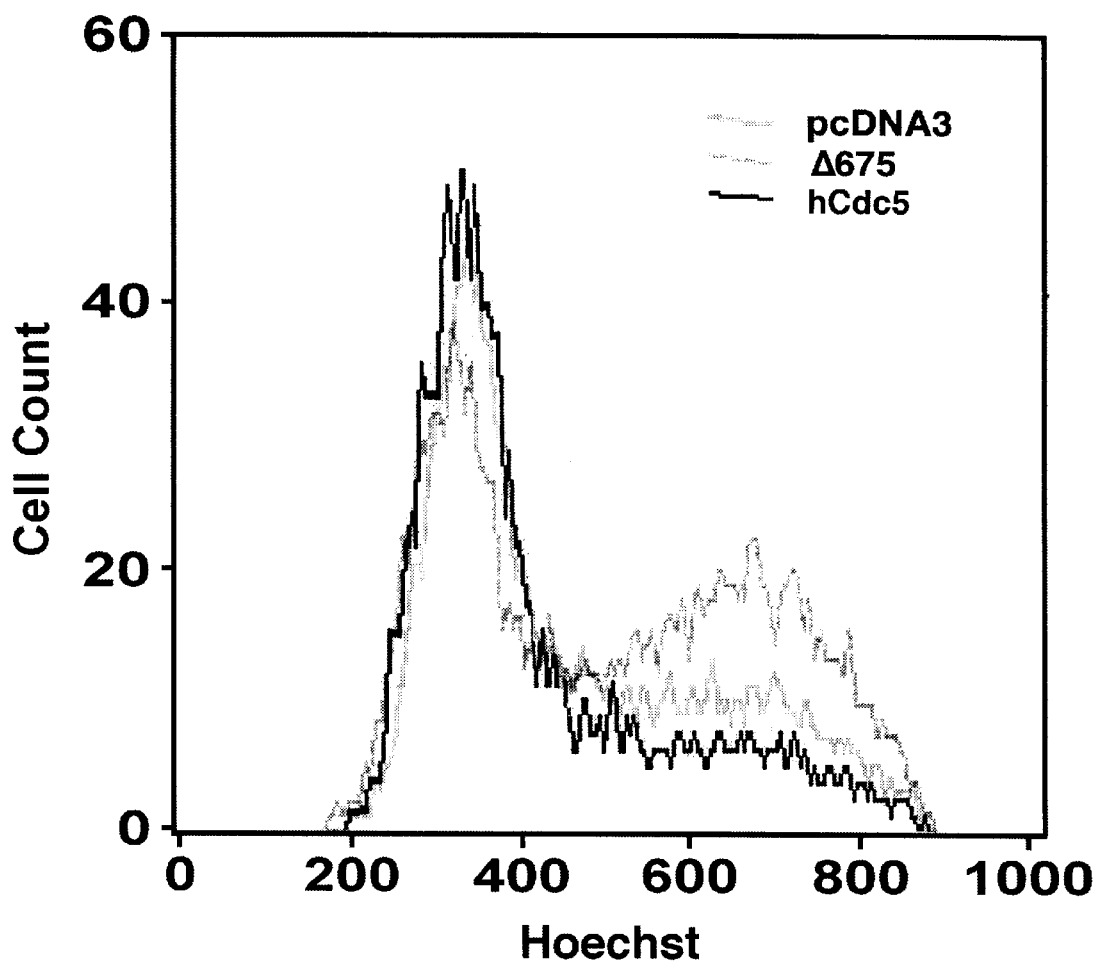
FIG. 11 is a graph depicting the alteration of cell cycle distribution in asynchronous cultures resulting from expression of mutant Δ675. Actively dividing Jurkat cultures were co-transfected with a vector directing the expression of green fluorescent protein (GFP) and wild-type or mutant hCdc5, or empty vector (pcDNA3), and grown for 72 hours. $10^6$ cells were stained with propidium iodide and Hoechst 33342 to determine viability and DNA content, respectively, and $10^5$ cells were sorted by flow cytometry for GFP expression. $2 \times 10^4$ GFP-positive cells were analyzed for cell cycle distribution. A representative experiment is shown.
Figure 12:
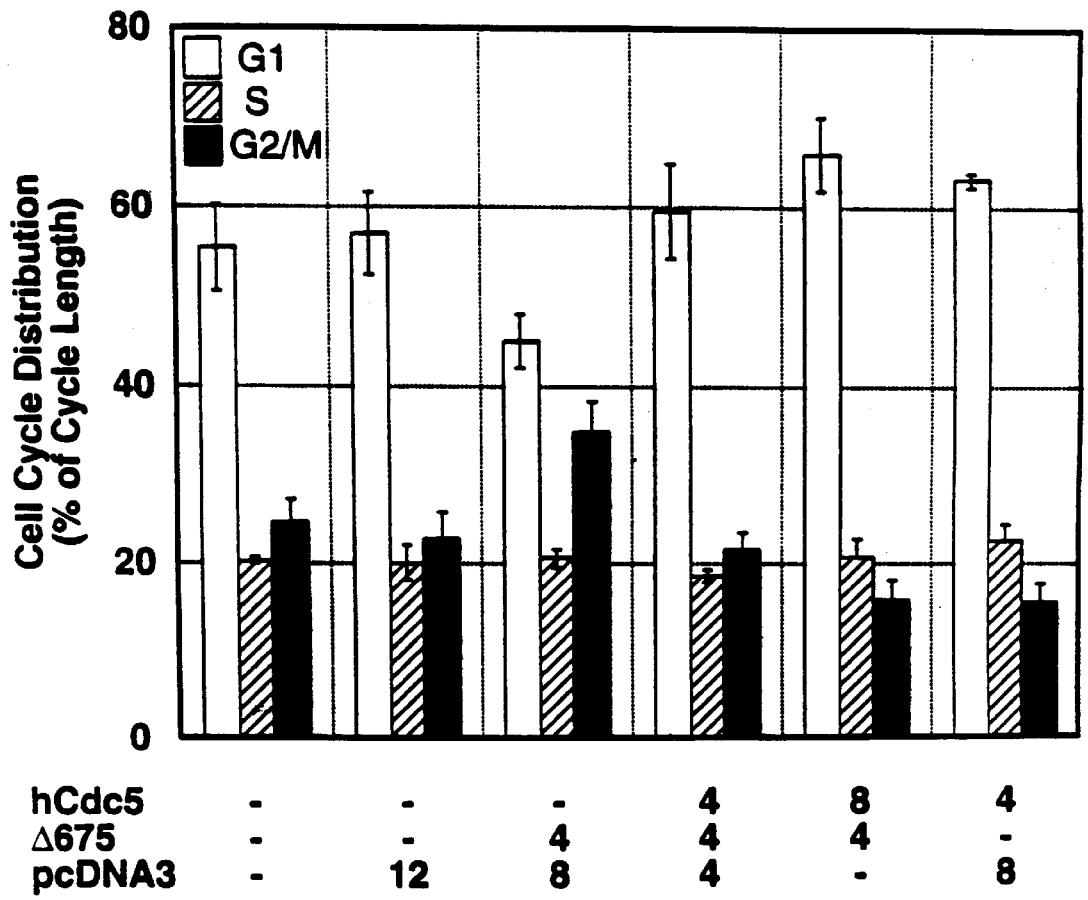
FIG. 12 is a graph depicting the delay of G2/M progress by mutant Δ675. Jurkat cells were transfected and analyzed as in FIG. 11. Cell cycle distributions for GFP-expressing transfectants were included in this analysis. Relative amounts of each vector used in transfection are shown. Data represent means from 3 experiments+/–sem. An increase or decrease in distribution toward G2/M is seen with mutant or wild-type hCdc5, respectively, compared with empty vector or untransfected cells.

To further examine the role of hCdc5 in G2 progression, we designed mutants which were predicted to inhibit the cellular effects of hCdc5 in a dominant negative manner. One mutant, designated, Δ675 contained the DNA binding and nuclear localization domains of hCdc5 but lacked its putative transcriptional activation domain (FIG. 10). This mutant should compete with wild-type hCdc5 in binding to its as yet unidentified target promoters but should fail to activate them. The human T cell Leukemia line (Jurkat) was co-transfected with vector containing either wild-type hCdc5, mutant Δ675, or vector alone and with a plasmid directing the constitutive expression of green fluorescent protein (GFP) as a marker for transfection (Iavarone, A. et al., Nature 387: 417–422 (1997)). Cells transfected with the Δ675 DNA expressed a protein of the expected molecular weight by immunoblot, and immunostaining confirmed that the expressed protein localized to the nucleus. GFP-positive cells in asynchronously dividing cultures were analyzed for cell cycle distribution by flow cytometry (FIG. 11). Cells expressing Δ675 mutant accumulated in G2/M (FIGS. 4B and 5), while cells transfected with the empty vector had a phase distribution similar to untransfected cells. Cultures transfected with wild-type hCdc5 distributed toward G1, as would be predicted from experiments with stable lines described above. Co-expression of wild-type hCdc5 with Δ675 titrated the mutant's effects of G2/M accumulation (FIG. 12), consistent with the mutant acting specifically in the hCdc5 pathway.

Figure 13:
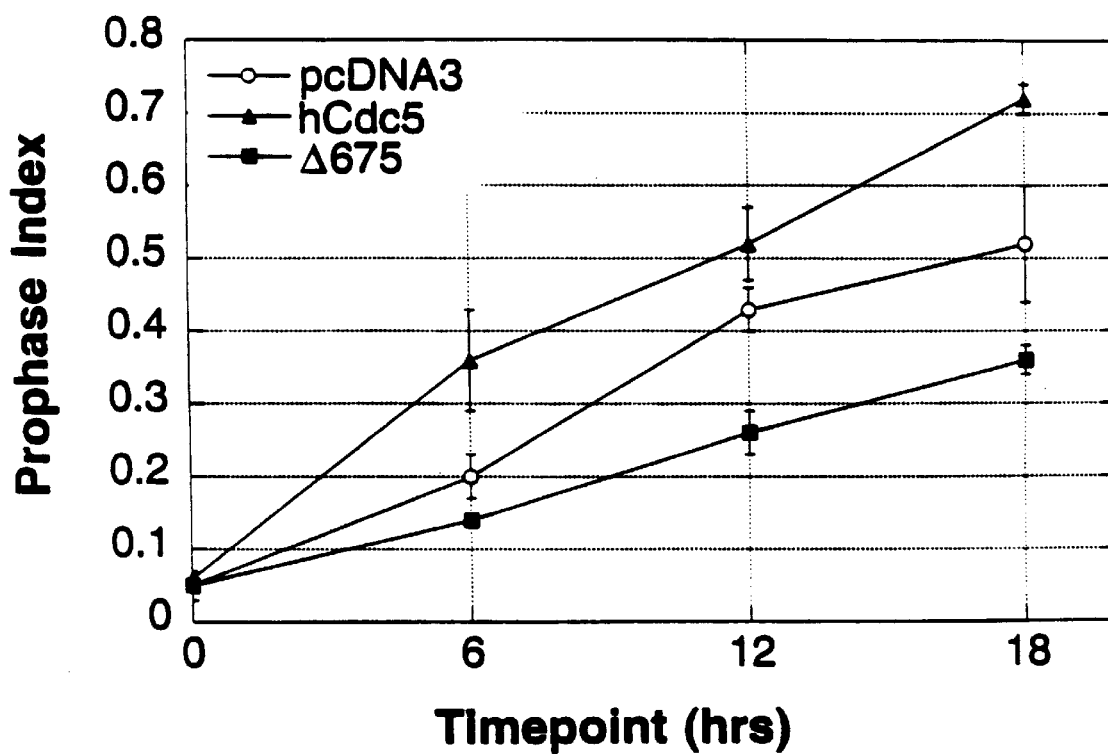
FIG. 13 is a graph depicting the specific delay of mitotic entry by mutant hCdc5. Jurkat cells were transfected as in FIG. 11. At 48 hours after transfection, nocodazole was added to 0.5 µg/ml, and cells were stained with Hoechst 33342 at timepoints indicated. For each experiment, slides containing $5 \times 10^3$ cells were prepared in triplicate from each transfection and 200 GFP-positive cells per slide were assessed for the presence of chromosomal condensation. Prophase index is plotted as a function of time. Data represent means from duplicate experiments+/−sem.

We next used mutant Δ675 to ask whether cells in which hCdc5's effects were inhibited were delayed in G2 or in mitosis. Jurkat cultures co-transfected as above were examined for chromosomal condensation at various times after exposure to nocodazole, which causes cell cycle arrest prior to metaphase in these cells (Krek, W. et al., Methods Enzymol. 254: 114–124 (1995); Kung, A. L. et al., Proc. Natl. Acad. Sci. U.S.A. 87: 9553–9557 (1990)). GFP-expressing cells transfected with Δ675 mutant exhibited a significantly slower rise in the fraction of cells in prophase over time compared with empty vector transfectants (FIG. 13). Cells expressing wild-type hCdc5 displayed a slightly faster rise in prophase index compared with empty vector, and a significantly accelerated increase compared with cells expressing the mutant. Since nocodazole disrupts mitosis shortly after chromosomal condensation, these results indicate that hCdc5 acts at least in part during interphase. Taken together with the flow cytometry data, these observations strongly indicate that hCdc5 regulates G2 progression and mitotic entry.

4. hCdc5 Expression is Not Cell Cycle-Dependent

Figure 14A:
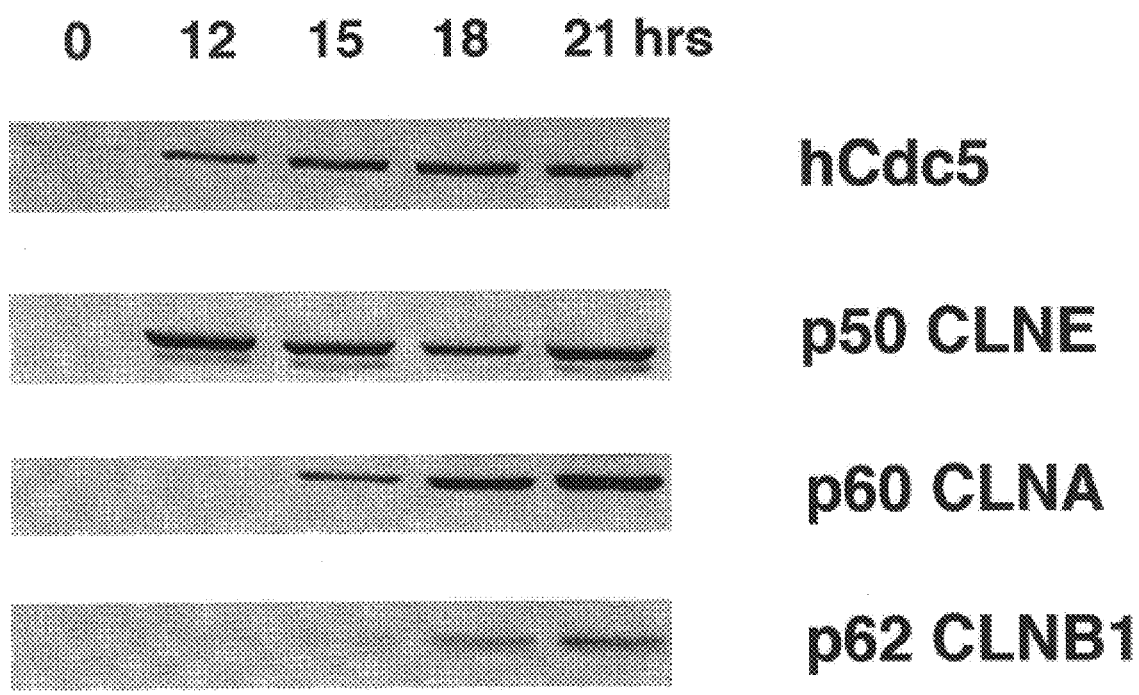
FIG. 14A is an immunoblot depicting temporal expression of endogenous hCdc5. BALBc/3T3 cultures were quiesced in low serum for 48 hours, then released with serum stimulation and harvested at indicated timepoints. Whole cell lysates were analyzed by immunoblotting with monoclonal antibody to the C-terminus of hCdc5, or polyclonal antibodies to murine cyclins E (p50 CLNE), A (p60 CLNA), or B1(p62 CLNB1).
Figure 14B:
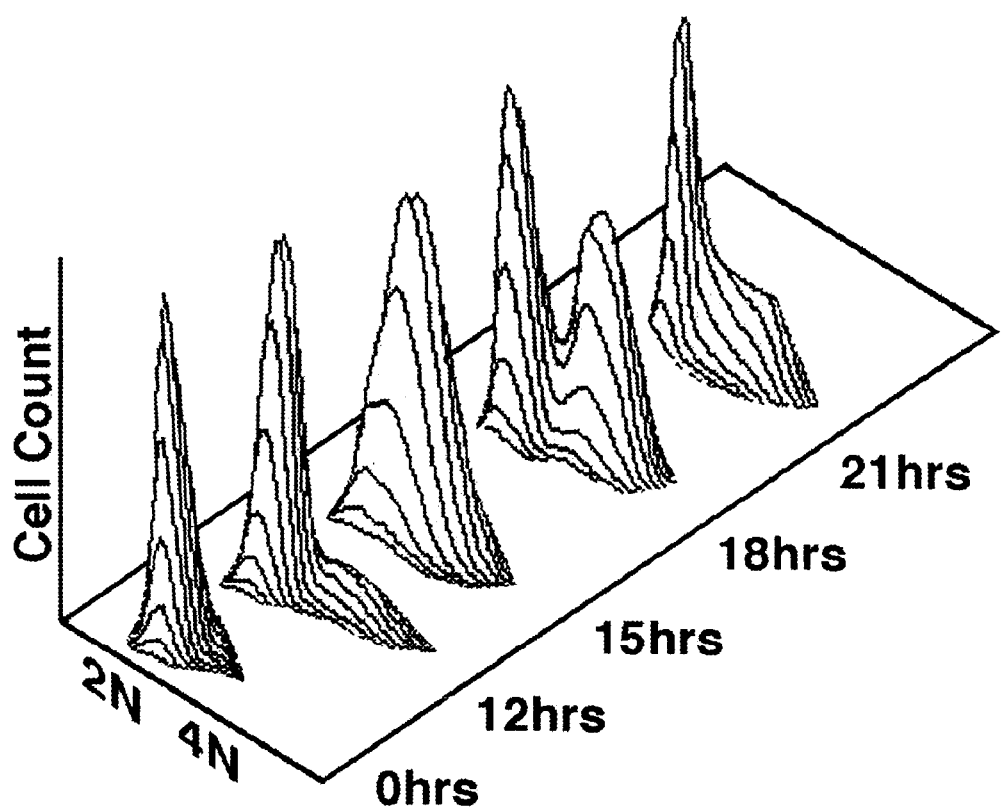
FIG. 14B is a graph depicting cells at each timepoint in FIG. 14A. Cells were fixed in ethanol, stained with propidium iodide, and evaluated by flow cytometry for DNA content distribution to confirm synchronization.

Many proteins controlling cell cycle progression are regulated at the level of expression and degradation (Morgan, D. O., Nature 374: 131–134 (1995)). We therefore asked whether expression of hCdc5 was cell cycle-dependent. BALBc/3T3 cells were synchronized in G0 by serum depletion, then released into G1. Whole cell lysates from cultures harvested at various times after release from quiescence were analyzed by immunoblotting for hCdc5 or specific cyclins (FIG. 14A). Cell cycle synchronization was confirmed by flow cytometry and analysis of DNA content (FIG. 14B). hCdc5 protein levels were low in quiescent cells, but increased rapidly upon serum stimulation and remained constant throughout the cell cycle. Immunolocalization studies showed that hCdc5 moved rapidly from the cytoplasm to the nucleus upon serum stimulation of quiescent cells, but in dividing cells hCdc5 remained in the nucleus throughout the cycle. Thus, hCdc5 is regulated at the level of subcellular location and protein expression in cells entering the division cycle, but not in actively dividing cells The results described above indicates hCdc5 might be regulated in two distinct ways. In quiescent cells, the rapid translocation of hCdc5 from cytoplasm to nucleus and upregulation of its expression upon addition of serum indicates regulation by extracellular signals. Available data do not as yet reveal a role for hCdc5 in G0 or G1, thus the functional result of hCdc5's early upregulation and nuclear localization is unclear. Without being limited to any one theory, hCdc5's movement to the nucleus might serve to promote its own expression in preparation for later cell cycle events. Such positive autoregulation has been described for c-Myc (Leone, G. et al., Nature 387: 422–426 (1997); Zornig, M. et al., Curr. Biol. 6: 1553–1556 91996)). Alternatively, localization and expression of hCdc5 might be regulated independently. Regardless of how hCdc5 comes to be expressed and localized in the nucleus of dividing cells, the data described above indicates that hCdc5 activity is not regulated at the level of expression or localization in actively dividing cells.

We previously demonstrated that hCdc5 becomes hyperphosphorylated in serum-stimulated COS-7 cells (Bernstein, H. S. et al., J. Biol. Chem. 272: 5833–5837 (1997)). Moreover, a X laevis homolog of hCdc5 recently was identified as an in vitro substrate of Cdc2 kinase (Stukenberg, P. T. et al., Curr. Biol. 7: 338–348 (1997)). The similarity between the weel phenotype in S. pombe and that of mammalian cells overexpressing hCdc5 is tantalizing in this context. These observations indicate that hCdc5 may be a substrate for and transcriptional effector of Cdc2 in mammalian cells, and predict its negative regulation by Weel and positive regulation by Cdc25B.

hCdc5, S. pombe Cdc5, and other Cdc5-like proteins are putative transcription factors by virtue of their primary structures (Bernstein, H. S. et al., J. Biol. Chem. 272: 5833–5837 (1997); Hirayama, T. et al., Proc. Natl. Acad. Sci. U.S.A. 93: 13371–13376 (1996); Ohi, R. et al., EMBO J. 13: 471–483 (1994); Stukenberg, P. T. et al., Curr. Biol. 7: 338–348 (1997); Wilson, R. et al., Nature 368: 32–38 (1994)). The genes that they regulate are unknown. As discussed above, it is possible that they are transcriptional effectors for Cdc2 kinase and regulate expression of genes necessary for G2 progression and mitotic entry. It also is possible that they act upstream of Cdc2, promoting its activation by regulating the expression of kinases and phosphatases that control Cdc2 (see above).

Thus, based on its primary structure, hCdc5 is almost certainly a DNA-binding protein and very likely regulates transcription (Bernstein, H. S. et al., J. Biol. Chem. 272: 5833–5837 (1997)). Overexpression of hCdc5 shortened G2 in mammalian cells and decreased cell size, presumably by bypassing a G2/M size checkpoint. A dominant negative hCdc5 mutant delayed mitotic entry. These findings strongly indicate that hCdc5 is a functional homolog of S. pombe Cdc5 and as such. These studies also confirm hCdc5, as the first described DNA binding protein which regulates mitotic entry in mammalian cells.

All references (including books, articles, papers, patents, and patent applications) cited herein are hereby expressly incorporated by reference in their entirety for all purposes.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

SEQUENCE LISTING

<160> NUMBER OF SEQ ID NOS: 12

<210> SEQ ID NO 1
<211> LENGTH: 802
<212> TYPE: PRT
<213> ORGANISM: Homo sapiens

<400> SEQUENCE: 1

```
Met Pro Arg Ile Met Ile Lys Gly Gly Val Trp Arg Asn Thr Glu Asp
  1               5                  10                  15

Glu Ile Leu Lys Ala Ala Val Met Lys Tyr Gly Lys Asn Gln Trp Ser
             20                  25                  30

Arg Ile Ala Ser Leu Leu His Arg Lys Ser Ala Lys Gln Cys Lys Ala
         35                  40                  45

Arg Trp Tyr Glu Trp Leu Asp Pro Ser Ile Lys Lys Thr Glu Trp Ser
     50                  55                  60

Arg Glu Glu Glu Glu Lys Leu Leu His Leu Ala Lys Leu Met Pro Thr
 65                  70                  75                  80

Gln Trp Arg Thr Ile Ala Pro Ile Ile Gly Arg Thr Ala Ala Gln Cys
                 85                  90                  95

Leu Glu His Tyr Glu Phe Leu Leu Asp Lys Ala Ala Gln Arg Asp Asn
            100                 105                 110

Glu Glu Glu Thr Thr Asp Asp Pro Arg Lys Leu Lys Pro Gly Glu Ile
        115                 120                 125

Asp Pro Asn Pro Glu Thr Lys Pro Ala Arg Pro Asp Pro Ile Asp Met
    130                 135                 140

Asp Glu Asp Glu Leu Glu Met Leu Ser Glu Ala Arg Ala Arg Leu Ala
145                 150                 155                 160

Asn Thr Gln Gly Lys Lys Ala Lys Arg Lys Ala Arg Glu Lys Gln Leu
                165                 170                 175

Glu Glu Ala Arg Arg Leu Ala Ala Leu Gln Lys Arg Arg Glu Leu Arg
            180                 185                 190

Ala Ala Gly Ile Glu Ile Gln Lys Lys Arg Lys Arg Lys Arg Gly Val
        195                 200                 205

Asp Tyr Asn Ala Glu Ile Pro Phe Glu Lys Lys Pro Ala Leu Gly Phe
    210                 215                 220

Tyr Asp Thr Ser Glu Glu Asn Tyr Gln Ala Leu Asp Ala Asp Phe Arg
225                 230                 235                 240

Lys Leu Arg Gln Gln Asp Leu Asp Gly Glu Leu Arg Ser Glu Lys Glu
                245                 250                 255

Gly Arg Asp Arg Lys Asp Lys Gln His Leu Lys Arg Lys Lys Glu
            260                 265                 270

Ser Asp Leu Pro Ser Ala Ile Leu Gln Thr Ser Gly Val Ser Glu Phe
        275                 280                 285

Thr Lys Lys Arg Ser Lys Leu Val Leu Pro Ala Pro Gln Ile Ser Asp
    290                 295                 300

Ala Glu Leu Gln Glu Val Val Lys Val Gly Gln Ala Ser Glu Ile Ala
305                 310                 315                 320

Arg Gln Thr Ala Glu Glu Ser Gly Ile Thr Asn Ser Ala Ser Ser Thr
                325                 330                 335

Leu Leu Ser Glu Tyr Asn Val Thr Asn Asn Ser Val Ala Leu Arg Thr
            340                 345                 350

Pro Arg Thr Pro Ala Ser Gln Asp Arg Ile Leu Gln Glu Ala Gln Asn
```

```
                355                 360                 365
Leu Met Ala Leu Thr Asn Val Asp Thr Pro Leu Lys Gly Gly Leu Asn
        370                 375                 380
Thr Pro Leu His Glu Ser Asp Phe Ser Gly Val Thr Pro Gln Arg Gln
385                 390                 395                 400
Val Val Gln Thr Pro Asn Thr Val Leu Ser Thr Pro Phe Arg Thr Pro
                405                 410                 415
Ser Asn Gly Ala Glu Gly Leu Thr Pro Arg Ser Gly Thr Thr Pro Lys
            420                 425                 430
Pro Val Ile Asn Ser Thr Pro Gly Arg Thr Pro Leu Arg Asp Lys Leu
            435                 440                 445
Asn Ile Asn Pro Glu Asp Gly Met Ala Asp Tyr Ser Asp Pro Ser Tyr
        450                 455                 460
Val Lys Gln Met Glu Arg Glu Ser Arg Glu His Leu Arg Leu Gly Leu
465                 470                 475                 480
Leu Gly Leu Pro Ala Pro Lys Asn Asp Phe Glu Ile Val Leu Pro Glu
                485                 490                 495
Asn Ala Glu Lys Glu Leu Glu Glu Arg Glu Ile Asp Asp Thr Tyr Ile
            500                 505                 510
Glu Asp Ala Ala Asp Val Asp Ala Arg Lys Gln Ala Ile Arg Asp Ala
            515                 520                 525
Glu Arg Val Lys Glu Met Lys Arg Met His Lys Ala Val Gln Lys Asp
        530                 535                 540
Leu Pro Arg Pro Ser Glu Val Asn Thr Glu Ile Leu Arg Pro Leu Asn
545                 550                 555                 560
Val Glu Pro Pro Leu Thr Asp Leu Gln Lys Ser Glu Glu Leu Ile Lys
                565                 570                 575
Lys Glu Met Ile Thr Met Leu His Tyr Asp Leu Leu His His Pro Tyr
            580                 585                 590
Glu Pro Ser Gly Asn Lys Lys Gly Lys Thr Val Gly Phe Gly Thr Asn
        595                 600                 605
Asn Ser Glu His Ile Thr Tyr Leu Glu His Asn Pro Tyr Glu Lys Phe
        610                 615                 620
Ser Lys Glu Glu Leu Lys Lys Ala Gln Asp Val Leu Val Gln Glu Met
625                 630                 635                 640
Glu Val Val Lys Gln Gly Met Ser His Gly Glu Leu Ser Ser Glu Ala
                645                 650                 655
Tyr Asn Gln Val Trp Glu Glu Cys Tyr Ser Gln Val Leu Tyr Leu Pro
                660                 665                 670
Gly Gln Ser Arg Tyr Thr Arg Ala Asn Leu Ala Ser Lys Lys Asp Arg
            675                 680                 685
Ile Glu Ser Leu Glu Lys Arg Leu Glu Ile Asn Arg Gly His Met Thr
        690                 695                 700
Thr Glu Ala Lys Arg Ala Ala Lys Met Glu Lys Lys Met Lys Ile Leu
705                 710                 715                 720
Leu Gly Gly Tyr Gln Ser Arg Ala Met Gly Leu Met Lys Gln Leu Asn
                725                 730                 735
Asp Leu Trp Asp Gln Ile Glu Gln Ala His Leu Glu Leu Arg Thr Phe
                740                 745                 750
Glu Glu Leu Lys Lys His Glu Asp Ser Ala Ile Pro Arg Arg Leu Glu
            755                 760                 765
Cys Leu Lys Glu Asp Val Gln Arg Gln Gln Glu Arg Glu Lys Glu Leu
        770                 775                 780
```

Gln His Arg Tyr Ala Asp Leu Leu Glu Lys Glu Thr Leu Lys Ser
785                 790                 795                 800

Lys Phe

<210> SEQ ID NO 2
<211> LENGTH: 51
<212> TYPE: PRT
<213> ORGANISM: Homo sapiens

<400> SEQUENCE: 2

Ile Lys Gly Gly Val Trp Arg Asn Thr Glu Asp Glu Ile Leu Lys Ala
1               5                   10                  15

Ala Val Met Lys Tyr Gly Lys Asn Gln Trp Ser Arg Ile Ala Ser Leu
            20                  25                  30

Leu His Arg Lys Ser Ala Lys Gln Cys Lys Ala Arg Trp Tyr Glu Trp
        35                  40                  45

Leu Asp Pro
    50

<210> SEQ ID NO 3
<211> LENGTH: 51
<212> TYPE: PRT
<213> ORGANISM: Schizosaccharomyces pombe

<400> SEQUENCE: 3

Leu Lys Gly Gly Ala Trp Lys Asn Thr Glu Asp Glu Ile Leu Lys Ala
1               5                   10                  15

Ala Val Ser Lys Tyr Gly Lys Asn Gln Trp Ala Arg Ile Ser Ser Leu
            20                  25                  30

Leu Val Arg Lys Thr Pro Lys Gln Cys Lys Ala Arg Trp Tyr Glu Trp
        35                  40                  45

Ile Asp Pro
    50

<210> SEQ ID NO 4
<211> LENGTH: 50
<212> TYPE: PRT
<213> ORGANISM: Homo sapiens

<400> SEQUENCE: 4

Val Lys Gly Pro Trp Thr Lys Glu Glu Asp Gln Lys Val Ile Glu Leu
1               5                   10                  15

Val Lys Lys Tyr Gly Thr Lys Gln Trp Thr Leu Ile Ala Lys His Leu
            20                  25                  30

Lys Gly Arg Leu Gly Lys Gln Cys Arg Glu Arg Trp His Asn His Leu
        35                  40                  45

Asn Pro
    50

<210> SEQ ID NO 5
<211> LENGTH: 50
<212> TYPE: PRT
<213> ORGANISM: Homo sapiens

<400> SEQUENCE: 5

Ile Lys Gly Pro Trp Thr Lys Glu Glu Asp Gln Lys Val Ile Glu Leu
1               5                   10                  15

Val Gln Lys Tyr Gly Pro Lys Arg Trp Ser Leu Ile Ala Lys His Leu
            20                  25                  30

```
Lys Gly Arg Ile Gly Lys Gln Cys Arg Glu Arg Trp His Asn His Leu
            35                  40                  45
Asn Pro
    50

<210> SEQ ID NO 6
<211> LENGTH: 50
<212> TYPE: PRT
<213> ORGANISM: Homo sapiens

<400> SEQUENCE: 6

Ile Lys Gly Pro Trp Thr Lys Glu Glu Asp Gln Lys Val Ile Glu Leu
 1               5                  10                  15
Val Gln Lys Tyr Gly Pro Lys Arg Trp Ser Val Ile Ala Lys His Leu
            20                  25                  30
Lys Gly Arg Ile Gly Lys Gln Cys Arg Glu Arg Trp His Asn His Leu
            35                  40                  45
Asn Pro
    50

<210> SEQ ID NO 7
<211> LENGTH: 123
<212> TYPE: PRT
<213> ORGANISM: Homo sapiens

<400> SEQUENCE: 7

Pro Leu Lys Gly Gly Leu Asn Thr Pro Leu His Glu Ser Asp Phe Ser
 1               5                  10                  15
Gly Val Thr Pro Gln Arg Gln Val Val Gln Thr Pro Asn Thr Val Leu
            20                  25                  30
Ser Thr Pro Phe Arg Thr Pro Ser Asn Gly Ala Glu Gly Leu Thr Pro
            35                  40                  45
Arg Ser Gly Thr Thr Pro Lys Pro Val Ile Asn Ser Thr Pro Gly Arg
 50                  55                  60
Thr Pro Leu Arg Asp Lys Leu Asn Ile Asn Pro Glu Asp Gly Met Ala
 65                  70                  75                  80
Asp Tyr Ser Asp Pro Ser Tyr Val Lys Gln Met Glu Arg Glu Ser Arg
                85                  90                  95
Glu His Leu Arg Leu Gly Leu Leu Gly Leu Pro Ala Pro Lys Asn Asp
                100                 105                 110
Phe Glu Ile Val Leu Pro Glu Asn Ala Glu Lys
            115                 120

<210> SEQ ID NO 8
<211> LENGTH: 107
<212> TYPE: PRT
<213> ORGANISM: Schizosaccharomyces pombe

<400> SEQUENCE: 8

Ser Val Thr Ile Glu Val Arg Asn Gln Leu Met Asn Arg Glu Gln Ser
 1               5                  10                  15
Ser Leu Leu Gly Gln Glu Ser Ile Pro Leu Gln Pro Gly Gly Thr Gly
            20                  25                  30
Tyr Thr Gly Val Thr Pro Ser His Ala Ala Asn Gly Ser Ala Leu Ala
            35                  40                  45
Ala Pro Gln Ala Thr Pro Phe Arg Thr Pro Arg Asp Thr Phe Ser Ile
 50                  55                  60
```

```
Asn Ala Ala Ala Glu Arg Ala Gly Arg Leu Ala Ser Glu Arg Glu Asn
 65                  70                  75                  80

Lys Ile Arg Leu Lys Ala Leu Arg Glu Leu Leu Ala Lys Leu Pro Lys
                 85                  90                  95

Pro Lys Asn Asp Tyr Glu Leu Met Glu Pro Arg
                100                 105

<210> SEQ ID NO 9
<211> LENGTH: 119
<212> TYPE: PRT
<213> ORGANISM: Homo sapiens

<400> SEQUENCE: 9

Pro Val Lys Thr Leu Pro Phe Ser Pro Ser Gln Phe Leu Asn Phe Trp
  1               5                  10                  15

Asn Lys Gln Asp Thr Leu Glu Leu Glu Ser Pro Ser Leu Thr Ser Thr
                 20                  25                  30

Pro Val Cys Ser Gln Lys Val Val Thr Thr Pro Leu His Arg Asp
                 35                  40                  45

Lys Thr Pro Leu His Gln Lys His Ala Ala Phe Val Thr Pro Asp Gln
 50                  55                  60

Lys Tyr Ser Met Asp Asn Thr Pro His Thr Pro Thr Pro Phe Lys Asn
 65                  70                  75                  80

Ala Lys Tyr Gly Pro Leu Lys Pro Leu Pro Gln Thr Pro His Leu Glu
                 85                  90                  95

Glu Asp Leu Lys Glu Val Leu Arg Ser Glu Ala Gly Ile Glu Leu Ile
                100                 105                 110

Ile Glu Asp Asp Ile Arg Pro
                115

<210> SEQ ID NO 10
<211> LENGTH: 123
<212> TYPE: PRT
<213> ORGANISM: Homo sapiens

<400> SEQUENCE: 10

Ile Leu Arg Lys Lys Arg Lys Met Arg Val Gly His Ser Pro Gly Ser
  1               5                  10                  15

Glu Leu Arg Asp Gly Ser Leu Asn Asp Gly Asn Met Ala Leu Lys
                 20                  25                  30

His Thr Pro Leu Lys Thr Leu Pro Phe Ser Pro Ser Gln Phe Asn
                 35                  40                  45

Thr Cys Pro Gly Asn Glu Gln Leu Asn Ile Glu Asn Pro Ser Phe Thr
 50                  55                  60

Ser Thr Pro Ile Cys Gly Gln Lys Ala Leu Ile Thr Thr Pro Leu His
 65                  70                  75                  80

Lys Glu Thr Thr Pro Lys Asp Gln Lys Glu Asn Val Gly Phe Arg Thr
                 85                  90                  95

Pro Thr Ile Arg Arg Ser Ile Leu Gly Thr Pro Arg Thr Pro Thr Pro
                100                 105                 110

Phe Lys Asn Ala Leu Ala Ala Gln Glu Lys Lys
        115                 120

<210> SEQ ID NO 11
<211> LENGTH: 2837
<212> TYPE: DNA
<213> ORGANISM: Homo sapiens
```

-continued

<400> SEQUENCE: 11

```
ggcacgagag gaagtggcgg ctttgagtcc ggtggcccaa tcgctgttac tacttctctg      60
aagctcctct cggctgcttg ccgagacacc ctgccgccaa gatgcctcga attatgatca     120
agggggggcgt atggaggaat accgaggatg aaattctgaa agcagcggta atgaaatatg    180
ggaaaaatca gtggtctagg attgcctcat tgctgcatag aaaatcagca aagcagtgca    240
aagccagatg gtatgaatgg ctggatccaa gcattaagaa gacagaatgg tccagagaag    300
aagaggaaaa actcttgcac ttggccaagt tgatgccaac tcagtggagg accattgctc    360
caatcattgg aagaacagcg gcccagtgct tagaacacta tgaatttctt ctggataaag    420
ctgcccaaag agacaatgaa gaggaaacaa cagatgatcc acgaaaactt aaacctggag    480
aaatagatcc aaatccagaa acaaaaccag cgcggcctga tccaattgat atggatgagg    540
atgaacttga gatgctttct gaagccgagg cccgcttggc taatactcag ggaaagaagg    600
ccaagaggaa agcaagagag aaacaattgg aagaagcaag acgtcttgct gccctccaaa    660
aaagaagaga acttcgagca gctggcatag aaattcagaa gaaagaaaaa aggaagagag    720
gagttgatta taatgccgaa atcccatttg aaaaaaagcc tgcccttggt ttttatgata    780
cttctgagga aaactaccaa gctcttgacg cagatttcag gaattaaga caacaggatc    840
ttgatgggga gctaagatct gaaaaagaag gaagagatag aaaaaaagac aaacagcatt    900
tgaaaaggaa aaagaatct gatttaccat cagctattct tcaaactagt ggtgtttctg    960
aatttactaa aagagaagc aaactagtac ttcctgcccc tcagatttca gatgcagaac   1020
tccaggaagt tgtaaaagta ggccaagcga gtgaaattgc acgtcaaact gccgaggaat   1080
ctggcataac aaattctgct tccagtacac ttttgtctga gtacaatgtc accaacaaca   1140
gcgttgctct tagaacacca cgaacaccag cttcccagga cagaattctg caggaagccc   1200
agaacctcat ggccctcacc aatgtggaca ccccattgaa aggtggactt aatacccccat   1260
tgcatgagag tgacttctca ggtgtaactc cacagcgaca agttgtacag actccaaaca   1320
cagttctctc tactccattc aggactcctt ctaatgagc tgaagggctg actccccgga   1380
gtggaacaac tcccaaacca gttattaact ctactccggg tagaactcct cttcgagaca   1440
agttaaacat taatcccgag gatggaatgg cagactatag tgatccctct tacgtgaagc   1500
agatggaaag agaatcccga gaacatctcc gtttagggtt gttgggcctt cctgccccta   1560
agaatgattt tgaaattgtt ctaccagaaa atgccgagaa ggagctggaa gaacgtgaaa   1620
tagatgatac ttacattgaa gatgctgctg atgtggatgc tcgaaagcag gccatacgag   1680
atgcagagcg tgtaaaggaa atgaaacgaa tgcataaagc tgtccagaaa gatctgccaa   1740
gaccatcaga gtaaatgaa actattctaa gaccccttaaa tgtagaaccg cctttaacag   1800
atttacagaa aagtgaagaa ctaatcaaaa agaaatgat cacaatgctt cattatgacc   1860
ttctacatca ccccttatgaa ccatctggaa ataaaaaagg caaaactgta gggtttggta   1920
ccaataattc agagcacatt acctatctgg aacataatcc ttatgaaaag ttctccaaag   1980
aagagctgaa aaaggcccag gatgttttgg tgcaggagat ggaagtggtt aaacaaggaa   2040
tgagccatgg agagctctca agtgaagctt ataaccaggt gtgggaagaa tgctacagtc   2100
aagtttata tcttcctggg cagagccgct acacacgggc caatctggct agtaaaaagg   2160
acagaattga atcacttgaa aagaggctcg agataaacag gggtcacatg acgacagaag   2220
ccaagagggc tgcaaagatg gaaaagaaga tgaaattttt gcttgggggt taccagtctc   2280
gtgctatggg gctcatgaaa cagttgaatg acttatggga ccaaattgaa caggctcact   2340
```

```
tggagttacg cacttttgaa gaactcaaga aacatgaaga ttctgctatt ccccggaggc    2400
tagagtgtct aaaagaagac gttcagcgac aacaagaaag agaaaaggaa cttcaacata    2460
gatatgctga tttgctgctg gagaaagaga ctttaaagtc aaaattctga agtacagttt    2520
atattctgtc acaggattaa ttaattgccg gttttcatac tctagaaggc tgaaactgat    2580
gtttatcttc attgacaaat ttacccacca tctgtggttt ttcagttgtt tattttaaat    2640
gatatcgatc ttacacattc tgtgtataaa gaccttaact ccacaggacg gacattttag    2700
agtttaaatt attaaggcta tcattctttt agtaatgtca tatttgcaaa ctttttttagt   2760 tttggccttt aatttaaaaa gcctaatttt aaagtgctgc ctgtgagtaa ctcttgaata    2820 aaacaaaat ataaaaa                                                    2837
```

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: epitope
      for M2 monoclonal antibody

<400> SEQUENCE: 12

Asp Tyr Lys Asp Asp Asp Lys
1               5

What is claimed is:

1. An isolated nucleic acid comprising the sequence of FIG. 2D (SEQ ID No: 11).

2. The nucleic acid of claim 1, wherein the nucleic acid is cDNA.

3. An expression vector comprising the nucleic acid sequence of claim 1.

4. A host cell comprising the vector of claim 3.

5. An isolated nucleic acid encoding the hCdc5 protein comprising the sequence of SEQ ID No: 1.

6. An isolated oligonucleotide probe for hCdc5, comprising at least 15 consecutive nucleotides of SEQ ID NO: 11 or its complement, wherein the oligonucleotide probe is a member of an oligonucleotide probe pair for amplification of a hCdc5 sequence.

7. A method for detecting a mutation in a human Cdc5 gene comprising amplifying said gene using the oligonucleotide of claim 6 and screening said amplified gene for the presence of a mutation.

8. The oligonucleotide probe of claim 6, wherein the oligonucleotide probe comprises at least 30 consecutive nucleotides of SEQ ID NO: 11 or its complement.

9. An antisense nucleic acid comprising a nucleic acid sequence complementary to the nucleic acid sequence of FIG. 2D (SEQ ID NO: 11).

10. method of inhibiting translation of the mRNA of a human Cdc5 gene by a target cell comprising contacting said target cell with an oligonucleotide probe, wherein said probe comnrises at least 15 consecutive nucleotides of the complement of SEQ ID NO: 11, under conditions in which said oligonucleotide probe hybridizes to said mRNA, whereby translation of said mRNA is inhibited, wherein said contacting of said target cell occurs in vitro.

11. A method for detecting a human Cdc5 gene in a sample, said method comprising:

contacting said sample with an oligonucleotide probe for the hCdc5 gene, wherein said probe comprises at least 15 consecutive nucleotides of the sequence of SEQ ID No: 11, or its complement, under conditions in which said probe hybridizes to said human Cdc5 gene, and detecting the presence of the hybridized probe.

12. The method of claim 11, wherein said oligonucleotide probe comprises at least 30 consecutive nucleotides of the sequence of SEQ ID No: 11, or its complement.

13. The method of claim 11, wherein said oligonucleotide probe comprises at least 50 consecutive nucleotides of the sequence of SEQ ID No: 11, or its complement.

14. A method for detecting a hCdc5 mRNA in a sample, said method comprising:

contacting said sample with an oligonucleotide probe for the hCdc5 gene, wherein said probe comprises at least 15 consecutive nucleotides of the complement of the sequence of SEQ ID No: 11 under conditions in which said probe hybridizes to said hCdc5 mRNA, and detecting the presence of the hybridized probe.

15. The method of claim 14, wherein said oligonucleotide probe comprises at least 30 consecutive nucleotides of the complement of the sequence of SEQ ID No: 11.

16. The method of claim 14, wherein said oligonucleotide probe comprises at least 50 consecutive nucleotides of the complement of the sequence of the SEQ ID No: 11.

17. An isolated oligonucleotide probe for hCdc5, comprising at least 15 consecutive nucleotides of the coding region of SEQ ID NO: 11, or the complement thereof.

18. The oligonucleotide probe of claim 17 comprising at least 30 consecutive nucleotides of the coding region of SEQ ID NO: 11 or the complement thereof.

* * * * *